(12) United States Patent
Chobotov

(10) Patent No.: US 11,723,668 B2
(45) Date of Patent: Aug. 15, 2023

(54) SYSTEMS AND METHODS WITH ANCHOR DEVICE FOR FIXATION OF FILLING STRUCTURES IN BLOOD VESSELS

(71) Applicant: Endologix LLC, Irvine, CA (US)

(72) Inventor: Michael Chobotov, Carlsbad, CA (US)

(73) Assignee: Endologix LLC, Irvine, CA (US)

( * ) Notice: Subject to any disclaimer, the term of this patent is extended or adjusted under 35 U.S.C. 154(b) by 95 days.

(21) Appl. No.: 17/058,055

(22) PCT Filed: May 30, 2019

(86) PCT No.: PCT/US2019/034734
§ 371 (c)(1),
(2) Date: Nov. 23, 2020

(87) PCT Pub. No.: WO2019/232263
PCT Pub. Date: Dec. 5, 2019

(65) Prior Publication Data
US 2021/0186514 A1   Jun. 24, 2021

Related U.S. Application Data

(60) Provisional application No. 62/678,956, filed on May 31, 2018.

(51) Int. Cl.
| | | |
|---|---|---|
| *A61B 17/12* | (2006.01) | |
| *A61F 2/07* | (2013.01) | |
| *A61B 17/00* | (2006.01) | |

(52) U.S. Cl.
CPC .. *A61B 17/12118* (2013.01); *A61B 17/12031* (2013.01); *A61B 17/12181* (2013.01);
(Continued)

(58) Field of Classification Search
CPC ........ A61B 17/12031; A61B 17/12118; A61B 17/12181; A61B 2017/00477;
(Continued)

(56) References Cited

U.S. PATENT DOCUMENTS 5,639,278 A * 6/1997 Dereume ................. A61F 2/07
  623/1.13
5,782,904 A * 7/1998 White ..................... A61F 2/958
  623/1.13
(Continued)

OTHER PUBLICATIONS

International Preliminary Report on Patentability dated Dec. 10, 2020, from application No. PCT/US2019/034734.
(Continued)

*Primary Examiner* — Ryan J. Severson
(74) *Attorney, Agent, or Firm* — Foley & Lardner LLP

(57) ABSTRACT

A system, for deployment in a blood vessel includes an anchor device having a stent and a suture loop that joins distal end portions of the stent. A first filling structure and a second filling structure are at least partially insertable through the suture loop to an area within the stent when the stent is in an expanded state. The anchor device has a size such that at least a portion of the first filling structure and at least a portion of the second filling structure protrude through openings in the anchor device to form a seal against a wall of the blood vessel when the first filling structure and the second filling structure have been at least partially inserted through the suture loop and have been filled. A method allows for repairing one or more blood vessels using the system.

18 Claims, 14 Drawing Sheets

(52) U.S. Cl.
CPC ...... *A61F 2/07* (2013.01); *A61B 2017/00477* (2013.01); *A61B 2017/1205* (2013.01); *A61F 2002/077* (2013.01); *A61F 2220/0016* (2013.01); *A61F 2220/0075* (2013.01); *A61F 2230/0054* (2013.01); *A61F 2250/0098* (2013.01)

(58) Field of Classification Search
CPC ....... A61B 2017/1205; A61F 2002/077; A61F 2/07; A61F 2220/016; A61F 2220/0075; A61F 2230/0054; A61F 2250/0098
See application file for complete search history.

(56) References Cited

U.S. PATENT DOCUMENTS

| | | | | |
|---|---|---|---|---|
| 6,042,605 | A * | 3/2000 | Martin | A61F 2/07 623/1.13 |
| 6,070,589 | A * | 6/2000 | Keith | A61F 2/07 606/198 |
| 6,077,296 | A * | 6/2000 | Shokoohi | A61F 2/966 623/1.2 |
| 6,290,731 | B1 * | 9/2001 | Solovay | A61F 2/07 623/1.35 |
| 7,550,004 | B2 * | 6/2009 | Bahler | A61F 2/07 623/1.48 |
| 7,763,066 | B2 * | 7/2010 | Parker | A61F 2/915 623/1.34 |
| 8,202,311 | B2 * | 6/2012 | Demetriades | A61F 2/97 623/1.13 |
| 8,679,171 | B2 * | 3/2014 | Deem | A61F 2/07 623/1.11 |
| 8,784,474 | B2 * | 7/2014 | Sargent, Jr. | A61F 2/06 623/1.23 |
| 8,808,355 | B2 * | 8/2014 | Barrand | A61F 2/856 623/1.13 |
| 8,945,199 | B2 * | 2/2015 | Ganpath | A61F 2/06 623/1.11 |
| 9,271,854 | B2 * | 3/2016 | White | A61F 2/885 |
| 9,504,555 | B2 * | 11/2016 | Hartley | A61F 2/07 |
| 9,757,263 | B2 * | 9/2017 | Roeder | A61F 2/95 |
| 10,028,831 | B2 * | 7/2018 | Morin | A61F 2/2418 |
| 10,092,426 | B2 * | 10/2018 | McHugo | A61F 2/90 |
| 10,864,095 | B2 * | 12/2020 | Bales, Jr. | A61F 2/844 |
| 10,898,201 | B2 * | 1/2021 | Herbowy | A61B 17/12136 |
| 2004/0015229 | A1 * | 1/2004 | Fulkerson | A61F 2/91 600/431 |
| 2004/0193245 | A1 * | 9/2004 | Deem | A61F 2/856 623/1.13 |
| 2004/0230289 | A1 * | 11/2004 | DiMatteo | A61F 2/07 623/1.13 |
| 2005/0273155 | A1 * | 12/2005 | Bahler | A61F 2/07 623/1.13 |
| 2006/0004436 | A1 * | 1/2006 | Amarant | A61F 2/89 623/1.15 |
| 2006/0025847 | A1 * | 2/2006 | Parker | A61F 2/91 623/1.15 |
| 2006/0287676 | A1 | 12/2006 | Prajapati et al. | |
| 2007/0027526 | A1 | 2/2007 | Demetriades et al. | |
| 2007/0043425 | A1 * | 2/2007 | Hartley | A61F 2/07 623/1.13 |
| 2007/0179600 | A1 * | 8/2007 | Vardi | A61F 2/07 623/1.44 |
| 2009/0012356 | A1 | 1/2009 | Dann et al. | |
| 2009/0287145 | A1 * | 11/2009 | Cragg | A61F 2/07 604/103.03 |
| 2009/0318949 | A1 * | 12/2009 | Ganpath | A61F 2/06 606/192 |
| 2010/0036360 | A1 * | 2/2010 | Herbowy | A61F 2/07 600/300 |
| 2011/0093058 | A1 * | 4/2011 | Vardi | A61L 27/507 623/1.15 |
| 2011/0125244 | A1 * | 5/2011 | Roeder | A61F 2/95 623/1.11 |
| 2012/0041538 | A1 | 2/2012 | White et al. | |
| 2012/0310327 | A1 | 12/2012 | McHugo | |
| 2013/0030515 | A1 * | 1/2013 | Vardi | A61L 27/50 623/1.13 |
| 2014/0148888 | A1 * | 5/2014 | Barrand | A61B 17/12131 623/1.2 |
| 2015/0005810 | A1 | 1/2015 | Center et al. | |
| 2015/0148892 | A1 * | 5/2015 | Ganpath | A61F 2/06 623/1.42 |
| 2017/0231764 | A1 | 8/2017 | Morin et al. | |
| 2018/0028192 | A1 | 2/2018 | Herbowy et al. | |
| 2019/0151070 | A1 * | 5/2019 | Chobotov | A61F 2/07 |
| 2021/0186514 | A1 * | 6/2021 | Chobotov | A61F 2/954 |
| 2021/0353403 | A1 * | 11/2021 | Chobotov | A61F 2/07 |

OTHER PUBLICATIONS

International Search Report and Written Opinion dated Aug. 15, 2019, from application No. PCT/US2019/034734.

\* cited by examiner

```
┌─────────────────────────────────────────────────────────────────────────┐
│ Choose an anchor device from among a plurality of anchor devices of     │
│ different sizes based on a diameter of a proximal neck region of an     │
│ aneurysm                                                                │
└─────────────────────────────────────────────────────────────────────────┘
                                                                      400
                                    │
                                    ▼
┌─────────────────────────────────────────────────────────────────────────┐
│ Deploy the anchor device that includes a stent and a suture loop that   │
│ joins distal end portions of the stent                                  │
│  ┌───────────────────────────────────────────────────────────────────┐  │
│  │ Fix barbs of the anchor device to a wall of an aorta above renal  │  │  401
│  │ arteries                                                          │  │
│  └───────────────────────────────────────────────────────────────────┘  │
│                                                                    402  │
└─────────────────────────────────────────────────────────────────────────┘
                                    │
                                    ▼
┌─────────────────────────────────────────────────────────────────────────┐
│ Insert a first filling structure at least partially through the suture  │
│ loop                                                                    │
│  ┌───────────────────────────────────────────────────────────────────┐  │
│  │ View radiopaque material on the suture loop to aid the insertion  │  │
│  │ of the first filling structure at least partially through the     │  │
│  │ suture loop                                                  404  │  │  403
│  └───────────────────────────────────────────────────────────────────┘  │
│  ┌───────────────────────────────────────────────────────────────────┐  │
│  │ Insert a proximal end of the first filling structure at least 20  │  │
│  │ mm past the suture loop and entirely below the renal arteries    │  │
│  │                                                              405  │  │
│  └───────────────────────────────────────────────────────────────────┘  │
└─────────────────────────────────────────────────────────────────────────┘
                                    │
                                    ▼
┌─────────────────────────────────────────────────────────────────────────┐
│ Insert a second filling structure at least partially through the suture │
│ loop                                                                    │
│  ┌───────────────────────────────────────────────────────────────────┐  │
│  │ View radiopaque material on the suture loop to aid the insertion  │  │
│  │ of the second filling structure at least partially through the    │  │  406
│  │ suture loop                                                  407  │  │
│  └───────────────────────────────────────────────────────────────────┘  │
│  ┌───────────────────────────────────────────────────────────────────┐  │
│  │ Insert a proximal end of the second filling structure at least 20 │  │
│  │ mm past the suture loop and entirely below the renal arteries    │  │
│  │                                                              408  │  │
│  └───────────────────────────────────────────────────────────────────┘  │
└─────────────────────────────────────────────────────────────────────────┘
                                    │
                                    ▼
┌─────────────────────────────────────────────────────────────────────────┐
│ Fill the first filling structure to cause one or more portions of the   │
│ first filling structure to protrude through one or more openings        │
│ bounded by one or more stent struts of the stent and at least a         │
│ portion of the suture loop                                              │
│  ┌───────────────────────────────────────────────────────────────────┐  │  409
│  │ Fill the first filling structure with a polymer that sets after   │  │
│  │ the one or more portions of the first filling structure have      │  │
│  │ protruded through the one or more openings so as to lock the      │  │
│  │ first filling structure to the anchor device              410     │  │
│  └───────────────────────────────────────────────────────────────────┘  │
└─────────────────────────────────────────────────────────────────────────┘
                                    │
                                    ▼
┌─────────────────────────────────────────────────────────────────────────┐
│ Fill the second filling structure to cause one or more portions of the  │
│ second filling structure to protrude through a corresponding one or     │
│ more openings in a side of the stent                                    │
│  ┌───────────────────────────────────────────────────────────────────┐  │  411
│  │ Fill the second filling structure to cause the second filling     │  │
│  │ structure to form a seal with the first filling structure both    │  │
│  │ inside of the stent and outside of the stent              412     │  │
│  └───────────────────────────────────────────────────────────────────┘  │
└─────────────────────────────────────────────────────────────────────────┘
```

FIG. 7

SYSTEMS AND METHODS WITH ANCHOR DEVICE FOR FIXATION OF FILLING STRUCTURES IN BLOOD VESSELS

CROSS-REFERENCE TO RELATED PATENT APPLICATIONS

This application is a national stage application under 35 U.S.C. § 371 of International Application No. PCT/US2019/034734, filed on May 30, 2019, which claims priority from U.S. Provisional Patent App. Ser. No. 62/678,956, filed May 31, 2018, the entire contents of which are incorporated by reference herein.

FIELD

Embodiments disclosed herein relate generally to systems with stents and filling structures for use in blood vessels and to methods of using systems with stents and filling structures in blood vessels. Various embodiments relate to expandable prosthesis and methods for treating abdominal and other aneurysms.

BACKGROUND

Aneurysms are enlargements or bulges in blood vessels that are often prone to rupture and which therefore present a serious risk to a patient. Aneurysms may occur in any blood vessel but are of particular concern when they occur in the cerebral vasculature or the patient's aorta.

Abdominal aortic aneurysms (AAA's) are classified based on their location within the aorta as well as their shape and complexity. Aneurysms that are found below the renal arteries are referred to as infrarenal abdominal aortic aneurysms. Suprarenal abdominal aortic aneurysms occur above the renal arteries. Thoracic aortic aneurysms (TAA's) occur in the ascending, transverse, or descending part of the upper aorta. Infrarenal aneurysms are the most common, representing about 70% of all aortic aneurysms. Suprarenal aneurysms are less common, representing about 20% of the aortic aneurysms. Thoracic aortic aneurysms are the least common and often the most difficult to treat.

The most common form of aneurysm is "fusiform," where the enlargement extends about the entire aortic circumference. Less commonly, the aneurysms may be characterized by a bulge on one side of the blood vessel attached at a narrow neck. Thoracic aortic aneurysms are often dissecting aneurysms caused by hemorrhagic separation in the aortic wall, usually within the medial layer. A type of treatment for each of these types and forms of aneurysm is open surgical repair. Open surgical repair is quite successful in patients who are otherwise reasonably healthy and free from significant co-morbidities. Such open surgical procedures are problematic, however, since access to the abdominal and thoracic aortas is difficult to obtain and because the aorta must be clamped off, placing significant strain on the patient's heart.

Endoluminal grafts have come into widespread use for the treatment of aortic aneurysms in patients. In general, endoluminal repairs access the aneurysm "endoluminally" through either or both iliac arteries in the groin. The grafts are then implanted. Successful endoluminal procedures have a much shorter recovery period than open surgical procedures. Various endoluminal aortic aneurysm repairs, however, suffer from a number of limitations. Some endoluminal repair patients experience leakage at a proximal juncture, which is an attachment point closest to the heart. Another problem has been graft migration. In instances where the graft migrates or slips from its intended position, open surgical repair is sometimes required. This is a particular problem since the patients receiving the endoluminal grafts are often those who are not considered good candidates for open surgery.

SUMMARY OF THE DISCLOSURE

A system in accordance with an embodiment for deployment in a blood vessel includes an anchor device. The anchor device includes a stent and a suture loop that joins distal end portions of the stent. In various embodiments, the suture loop includes a plurality of suture segments. In various embodiments, the plurality of suture segments are arranged in a polygonal arrangement. In some embodiments, the stent includes a plurality of v-shaped stent elements that each have two stent struts that meet at a bone shaped apex around which the suture loop is wrapped. Also, in some embodiments, the suture loop is wrapped around each of the distal end portions of the stent so as to join the distal end portions of the stent.

In various embodiments, the anchor device includes barbs for attachment to the blood vessel. In various embodiments, the anchor device further includes radiopaque material positioned on at least a portion of the suture loop. In some embodiments, the stent is expandable to an expanded state, and the anchor device is configured such that when the stent is in the expanded state a diameter of a proximal aperture of the stent is greater than a diameter of a distal aperture of the stent that is bounded by the suture loop. Also, in some embodiments, the anchor device is configured such that when the stent is in the expanded state the diameter of the distal aperture of the stent is at least 5% smaller than the diameter of the proximal aperture of the stent. In some embodiments, the anchor device is configured such that when the stent is in the expanded state the diameter of the distal aperture of the stent is no less than 25% smaller than the diameter of the proximal aperture of the stent.

In various embodiments, the system further includes a first filling structure and a second filling structure. In various embodiments, the stent is expandable to an expanded state, and the first filling structure and the second filling structure are at least partially insertable through the suture loop to an area within the stent when the stent is in the expanded state. In some embodiments, the anchor device has a size such that at least a portion of the first filling structure and at least a portion of the second filling structure protrude through openings in the anchor device when the first filling structure and the second filling structure have been at least partially inserted through the suture loop and have been filled. In some embodiments, the openings in the anchor device are bounded by stent struts of the stent and the suture loop. Also, in some embodiments, the first filling structure and the second filling structure are sealable against each other and are lockable onto the anchor device when filled.

In various embodiments, the stent has a sufficient length such that the first filling structure and the second filling structure are deployable when extending at least 20 mm within the stent. In some embodiments, the anchor device includes barbs that are attachable to a wall of an aorta above renal arteries, and the anchor device has a size such that at least a portion of the first filling structure and at least a portion of the second filling structure protrude through openings in the anchor device to contact a wall of the aorta below the renal arteries when the barbs have been attached to the aorta above the renal arteries and the first filling structure and the second filling structure have been at least partially inserted through the suture loop and have been filled.

In various embodiments, the suture loop is configured to at least partially constrain the first filling structure and the second filling structure when the first filling structure and the second filling structure have been at least partially inserted through the suture loop and have been filled. In some embodiments, the first filling structure is deployable to provide a first lumen for blood flow from an aorta to a first iliac artery, and the second filling structure is deployable to provide a second lumen for blood flow from the aorta to a second iliac artery. Also, in some embodiments, the stent includes a plurality of stent struts that are each made of a nickel-titanium alloy, and the suture loop is made of thread.

A method in accordance with an embodiment for repairing one or more blood vessels includes deploying an anchor device that has a stent and a suture loop that joins distal end portions of the stent, inserting a first filling structure at least partially through the suture loop, and filling the first filling structure to cause one or more portions of the first filling structure to protrude through one or more openings bounded by one or more stent struts of the stent and at least a portion of the suture loop. In various embodiments, the method further includes inserting a second filling structure at least partially through the suture loop, and filling the second filling structure to cause one or more portions of the second filling structure to protrude through a corresponding one or more openings in a side of the stent.

In various embodiments, the one or more portions of the first filling structure and the one or more portions of the second filling structure contact a wall of a blood vessel of the one or more blood vessels to form a seal against the wall. In various embodiments, the anchor device is deployed using a first guidewire that passes through a first iliac artery, the first filling structure is deployed using the first guidewire, and the second filling structure is deployed using a second guidewire that is separate from the first guidewire and that passes through a second iliac artery. In some embodiments, the anchor device further includes radiopaque material on at least a portion of the suture loop, and the method further includes viewing the radiopaque material to aid the insertion of the first filling structure at least partially through the suture loop and to aid the insertion of the second filling structure at least partially through the suture loop.

In various embodiments, the anchor device is deployed at least partially in a proximal neck region of an aneurysm and, after deployment of the anchor device, a distal aperture of the stent that is bounded by the suture loop has a diameter that is at least 5% smaller than a diameter of the proximal neck region of the aneurysm. In some embodiments, the one or more blood vessels includes an aorta, the anchor device further includes barbs, deploying the anchor device includes fixing the barbs to a wall of the aorta above renal arteries, and after deployment of the anchor device the stent extends down in the aorta past the renal arteries and has a length below the renal arteries that is at least 20 mm. Also, in some embodiments, inserting the first filling structure at least partially through the suture loop includes inserting a proximal end of the first filling structure at least 20 mm past the suture loop and entirely below the renal arteries.

In various embodiments, filling the first filling structure includes filling the first filling structure with a polymer that sets after the one or more portions of the first filling structure have protruded through the one or more openings so as to lock the first filling structure to the anchor device. In various embodiments, the first filling structure is filled with a polymer, and the first filling structure is at least partially constrained by the suture loop when the first filling structure is filled with the polymer. In some embodiments, the one or more blood vessels include an aorta having an aneurysm, and the method further includes choosing the anchor device from among a plurality of anchor devices of different sizes based on a diameter of a proximal neck region of the aneurysm. Also, in some embodiments, the method further includes inserting a second filling structure at least partially through the suture loop, and filling the second filling structure to cause the second filling structure to form a seal with the first filling structure both inside of the stent and outside of the stent.

BRIEF DESCRIPTION OF THE DRAWINGS

FIG. 7 is a flowchart of a method in accordance with an embodiment for repairing one or more blood vessels.

DETAILED DESCRIPTION

Figure 1:
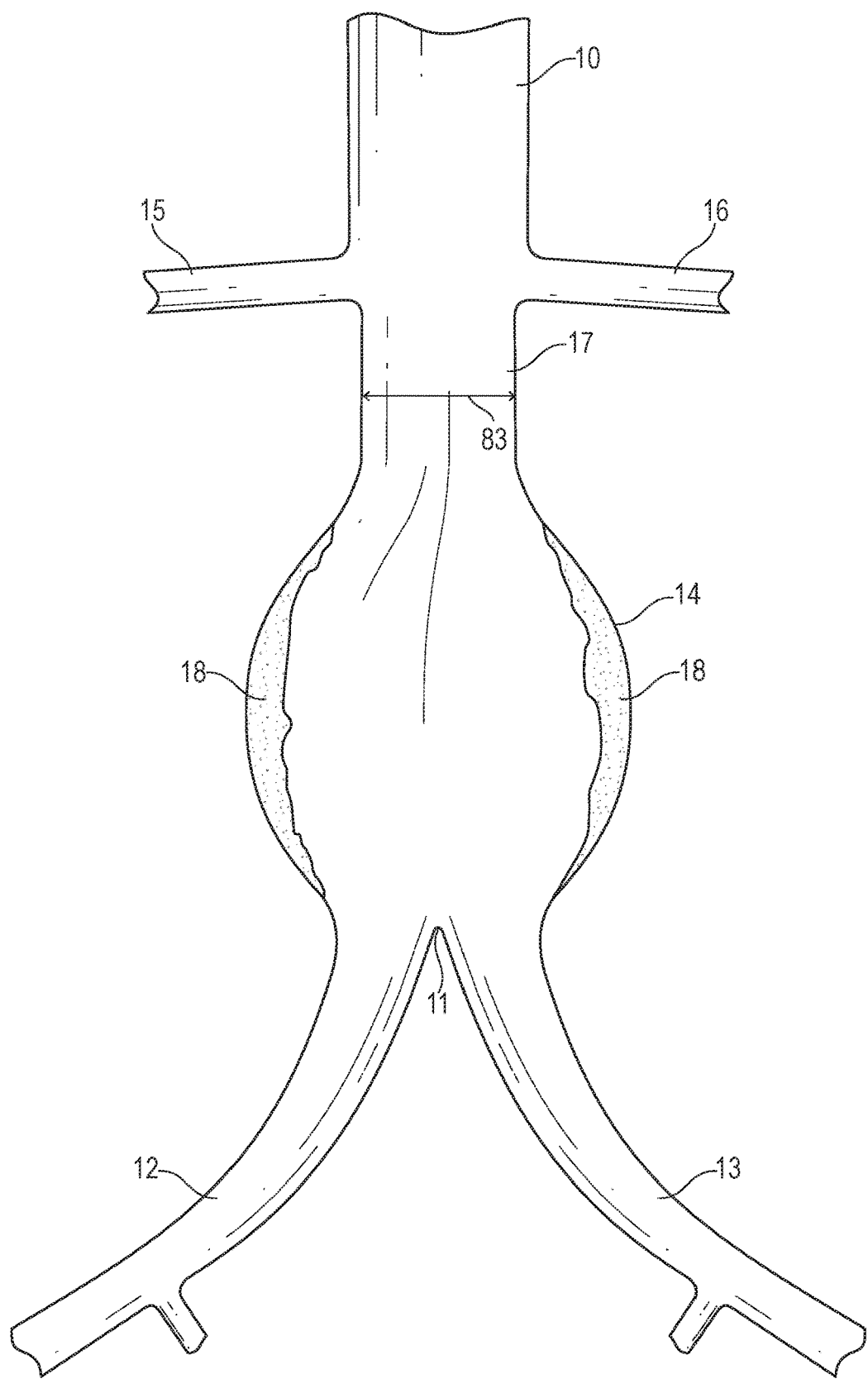
FIG. 1 is an illustration of a cross section of an example patient anatomy with an infrarenal aortic aneurysm.

In the following detailed description, reference is made to the accompanying drawings, which form a part hereof. In the drawings, similar symbols typically identify similar items, unless context dictates otherwise. The illustrative embodiments described in the detailed description and drawings are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure. With regard to embodiments of anchor devices and filling structures discussed herein, such as in endoluminal prosthesis systems, and components thereof, that are insertable into a patient, the term "proximal" refers to a location to be towards a patient's heart and the term "distal" refers to a location to be away from the patient's heart in a direction of blood flow.

Certain embodiments described herein are directed to systems, methods, and apparatuses to treat lesions, aneurysms, or other defects in blood vessels such as the aorta, including, but not limited to, the thoracic, ascending, and abdominal aorta, and the iliac arteries and renal arteries. However, the systems, methods, and apparatuses may have application to other areas of the body, or to other fields, and such additional applications are intended to form a part of this disclosure. For example, it will be appreciated that the systems, methods, and apparatuses may have application to the treatment of blood vessels in animals. Various embodiments and/or aspects of the endoluminal prosthesis systems, methods, and apparatuses described herein can be applied to other parts of the body or may have other applications apart from the treatment of blood vessels such as the aorta, iliac arteries, and renal arteries. And, while specific embodiments may be described herein with regard to particular portions of the aorta, it is to be understood that the embodiments described can be adapted for use in other portions of the aorta or other portions of the body and are not limited to the aortic portions described.

A system in accordance with various embodiments for placement in at least one blood vessel includes a polymer endovascular aneurysm sealing (EVAS) device that has one or more filling structures, such as endobags, that allow for excluding an aneurysm by filling an aneurysm sac space with polymer contained in the one or more filling structures. The system also includes an anchor device to improve fixation of such an EVAS device to the anatomy of a patient by means of the discrete anchor device, which in various embodiments engages the EVAS device to secure the EVAS device in place.

In various embodiments, the anchor device is pre-deployed into an arterial segment, such as in a proximal neck of an abdominal aortic aneurysm (AAA), and the anchor device deployment is followed by the deployment of the EVAS device. In some embodiments for the treatment of AAA, the anchor device includes a stent with barbs at a proximal end and with the distal ends of the stent joined in a polygonal arrangement of suture segments that form a suture loop. In various embodiments, radiopaque material is included with the suture loop to improve the visibility of the suture loop and facilitate cannulation of an aperture of the suture loop formed by the suture segments. In various embodiments, such cannulation is needed to allow for the passing of a contralateral catheter through the anchor device for deployment of a filling structure. In some embodiments, an ipsilateral catheter for deployment of another filling structure is advanced over a primary guidewire that was used to pre-deploy the anchor device, so that no cannulation step is needed for the ipsilateral catheter in such a situation.

In various embodiments, a distal aperture of the anchor device is sized such that it is about 5% to 25% smaller in diameter than a proximal neck region of the aneurysm, such that the endobags can inflate and protrude through interstices or openings in the anchor device that are bounded by stent struts of the stent and suture segments of the suture loop. When the polymer sets in the endobags, the endobags become joined (geometrically locked or engaged) to the anchor device, which results in the entire system being attached to the artery, such as the aorta. The anchor device can be constructed with Nitinol or other materials, and may or may not include suture material. Such an anchor device can also be used at a distal landing site as well, such as in an iliac artery.

In various embodiments, only a barbed proximal portion of the stent structure is deployed proximal to the renal arteries so as to allow a significant length, such as at least about 20 mm to 30 mm of a proximal bag portion of each of the endobags to be deployed proximal to the suture loop yet distal to the renal arteries. This allows for sufficient length for the endobags to reach sufficient radial expansion and arterial wall contact. Since AAA neck diameters vary over a wide range that is typically 16 mm to 32 mm, a variety of sizes, such as 5 different proximal stent sizes of the anchor device are made available in various embodiments. This allows for a fairly consistent amount of lumen constriction to be achieved by the anchor device suture loop across a wide range of AAA neck diameters. In various embodiments, a staged delivery system is used to deploy the anchor device prior to the deployment of the endobags. In some embodiments, the anchor device is used in cases involving a visceral aortic segment, such as for endovascular aneurysm sealing in combination with chimney grafts (chEVAS).

FIG. 1 is an illustration of a cross section of an example patient anatomy with an infrarenal aortic aneurysm. In FIG. 1, an aorta 10 branches at an aortic bifurcation 11 into two iliac arteries 12 and 13. A sac of an aneurysm 14 denotes a bulged section of the aorta 10. As the name implies, the infrarenal aortic aneurysm is located below renal arteries 15 and 16. A segment of the aorta 10 between the renal arteries 15 and 16 and the sac of the aneurysm 14 is referred to as a proximal neck region 17. The proximal neck region 17 has a diameter 83 that can be different for different patients. Often mural thrombus 18 forms on an inside wall of the sac of the aneurysm 14.

Figure 2:
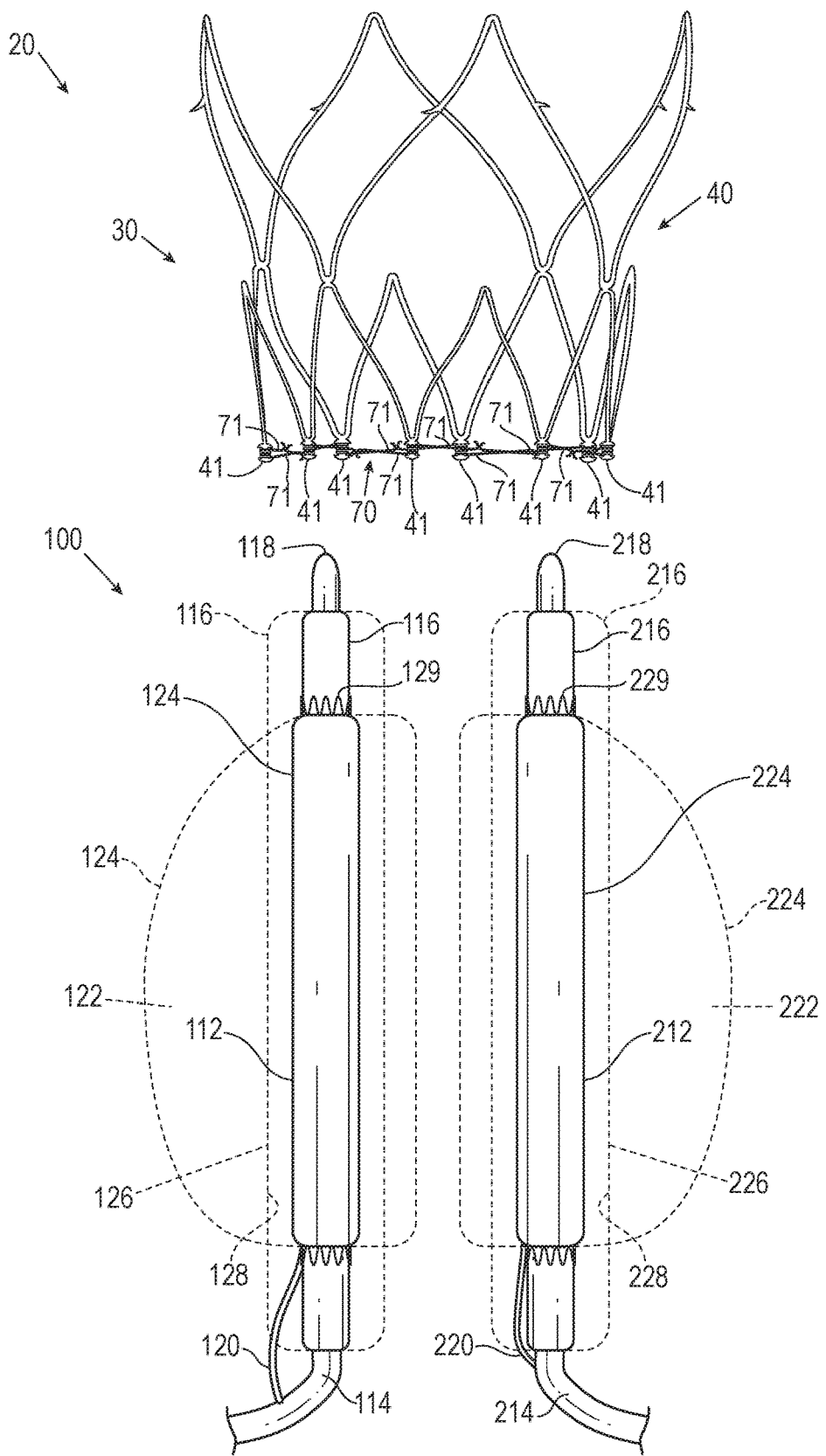
FIG. 2 shows a system in accordance with an embodiment for deployment in one or more blood vessels.

FIG. 2 is an illustration of a system 20 in accordance with an embodiment for deployment in one or more blood vessels, such as in the aorta 10 and the iliac arteries 12 and 13 shown in FIG. 1. With reference to FIG. 2, the system 20 includes an anchor device 30 and an endovascular aneurysm sealing (EVAS) device 100. The anchor device 30 includes a stent 40 and a suture loop 70. The suture loop 70 joins distal end portions 41 of the stent 40. In various embodiments, the suture loop 70 includes a plurality of suture segments 71 that are tied together to form the suture loop 70.

In various embodiments, the stent 40 has a tapered cylindrical body that is wider at a proximal end of the stent 40 and narrower at a distal end of the stent 40. In various embodiments, the stent 40 is formed from a suitable biocompatible material, such as a biocompatible alloy, a biocompatible metal, or a biocompatible polymer that may be a thermoplastic material. In some embodiments, the stent 40 is formed from a steel alloy, a cobalt-chromium alloy, a nickel-titanium alloy such as Nitinol, and/or any suitable type of shape memory alloy. The stent 40 is configured with an expandable geometry to expand from a compressed state to an expanded state. For example, in some embodiments, the stent 40 is a self-expanding stent. In some embodiments, the stent 40 is a balloon-expandable stent.

In various embodiments, the suture loop 70 includes the plurality of suture segments 71 that are each made of a suture material. In some embodiments, the suture material is a thread. In some embodiments, the suture material includes silk, polypropylene, polyester, and/or nylon. In some embodiments, the suture material is elastic. In some embodiments, the suture material includes a natural or synthetic fiber. In various embodiments, the suture loop 70 acts as a distal restraint member for the stent 40. In various embodiments, a distal restraint member made of a material different from a suture material can be used in place of the suture loop 70 and can join the distal end portions 41 of the stent 40.

The EVAS device 100 includes a filling structure 112 on a delivery catheter 114 having an expandable element 116, such as an inflatable balloon. In various embodiments, the filling structure 112 is a bag, such as an endobag or the like. In some embodiments, the EVAS device 100 includes a scaffold 129 that is expandable. The catheter 114 includes a guidewire lumen 118 for insertion of a guidewire, and also includes a filling tube 120 for delivering a filling medium or material to an internal space 122 of the filling structure 112. The internal space 122 is defined between an outer wall 124 and inner wall 126 of the filling structure 112. Upon inflation with the filling material or medium, the outer wall 124 will expand radially outwardly, as shown in broken line, as will the inner wall 126, also shown in broken line. Expansion of the inner wall 126 defines an internal lumen 128, which may also be defined by an expansion of the scaffold 129 in a case where the scaffold 129 is used. The expandable balloon or other structure 116 will be expandable to support an inner surface of the lumen 128 such as, for example, while the internal space 122 is being filled, as also shown in broken line in FIG. 2.

The EVAS device 100 further includes another filling structure 212 on a delivery catheter 214 having an expandable element 216, such as an inflatable balloon. In various embodiments, the filling structure 212 is a bag, such as an endobag or the like. In some embodiments, the EVAS device 100 includes a scaffold 229 that is expandable. The catheter 214 includes a guidewire lumen 218 for insertion of a guidewire, and also includes a filling tube 220 for delivering a filling medium or material to an internal space 222 of the filling structure 212. The internal space 222 is defined between an outer wall 224 and inner wall 226 of the filling structure 212. Upon inflation with the filling material or medium, the outer wall 224 will expand radially outwardly, as shown in broken line, as will the inner wall 226, also shown in broken line. Expansion of the inner wall 226 defines an internal lumen 228, which may also be defined by an expansion of the scaffold 229 in a case where the scaffold 229 is used. The expandable balloon or other structure 216 will be expandable to support an inner surface of the lumen 228 such as, for example, while the internal space 222 is being filled, as also shown in broken line in FIG. 2.

Various embodiments disclosed herein provide methods and systems for the endoluminal treatment of aneurysms, particularly aortic aneurysms including both abdominal aortic aneurysms (AAA's) and thoracic aortic aneurysms (TAA's). In various embodiments, the system 20 includes prostheses which comprise double-walled filling structures, such as the filling structures 112 and 212, which are pre-shaped and/or otherwise adapted to substantially fill an enlarged volume of an aneurysm, particularly a fusiform aneurysm, leaving one or more lumens in place for blood flow.

In various embodiments, the filling structures 112 and 212 include a generally toroidal structure with an outer wall, an inner wall, a potential space or volume between the outer and inner walls to be filled with a filling medium, and a generally tubular lumen inside of the inner wall which provides the blood flow lumen after the prosthesis has been deployed. In various embodiments, the shapes of the filling structures 112 and 212 are adapted to conform to the aneurysm being treated. In some instances, the filling structures 112 and 212 can be shaped for the aneurismal geometry of a particular patient using imaging and computer-aided design and fabrication techniques. In other instances, a family or collection of filling structures can be made having different geometries and sizes so that a treating physician may select a specific filling structure to treat a particular patient based on the size and geometry of that patient's aneurysm. In various embodiments, the outer wall 124 of the filling structure 112 and the outer wall 224 of the filling structure 212 are conformable to an inner surface of the aneurysm being treated while the inner wall 126 of the filling structure 112 and the inner wall 226 of the filling structure 212 are alignable with lumens of the blood vessels on either side of the prosthesis when the prosthesis is deployed.

In various embodiments, the filling structures 112 and 212 are formed from a non-compliant material, such as parylene, polyester (e.g., Dacron), polyethylene terephthalate (PET), polytetrafluoroethylene (PTFE), and/or a compliant material, such as silicone, polyurethane, latex, or combinations thereof. In some embodiments, the filling structures 112 and 212 are formed from expanded PTFE (ePTFE). The walls of the filling structures 112 and 212 may consist of a single layer or may comprise multiple layers which are laminated, glued, heat bonded, ultrasonically bonded, or otherwise formed together. Different layers may comprise different materials, including both compliant and/or non-compliant materials. The walls of the filling structures 112 and 212 may also be reinforced in various ways, including braid reinforcement layers, filament reinforcement layers, and/or the like.

In various embodiments, the scaffold 129 is expandable within the generally tubular lumen 128 which provides the blood flow after the filling structure 112 has been deployed in an aneurysm. Also, in various embodiments, the scaffold 229 is expandable within the generally tubular lumen 228 which provides the blood flow after the filling structure 212 has been deployed in an aneurysm.

In various embodiments, the scaffolds 129 and 229 are formed from an elastic material, particularly a spring steel or shape memory alloy, so that they may be delivered in a constrained configuration and allowed to expand to anchor within the respective generally tubular lumen 128 and 228 of the respective filling structure 112 and 212. Alternatively, the scaffolds 129 and 229 may be formed from a malleable metal or other material, such as stainless steel, and be delivered using a balloon catheter or other conventional stent expansion device, such as the respective expandable elements 116 and 216. The geometry of the scaffolds 129 and 229 may also vary considerably. In some embodiments, each scaffold 129 and 229 will extend over substantially an entire length of the respective inner wall of the respective generally tubular lumen 128 and 228 of the respective filling structure 112 and 212. In some embodiments, each scaffold 129 and 229 extends outwardly from at least one of the ends of the respective generally tubular lumen 128 and 228 into an adjacent blood vessel. Each scaffold 129 and 229 may also extend outwardly from both ends of the respective generally tubular lumen 128 and 228 as well as cover the entire inner wall surface of that respective lumen 128 and 228.

In other instances, multiple scaffold structures may be provided within a single generally tubular lumen of each of the filling structures 112 and 212. In such cases, the two or more scaffolds may be adapted to be placed in series and be overlapping. In other instances, scaffolds may be adapted to be spaced apart at either or both ends and optionally at regions between the ends. In some embodiments, each scaffold 129 and 229 includes a metal frame, at least a portion of which is covered by a polymeric membrane or other covering. In some instances, each scaffold 129 and 229 or portions thereof may be polymeric and optionally formed from a biodegradable polyester. It some embodiments, each of the scaffolds 129 and 229 is covered over at least those portions of the scaffold 129 and 229 which engage the inner wall of the respective generally tubular lumen 128 and 228 of the respective filling structure 112 and 212. The scaffolds 129 and 229 and/or their covers may be coated with, impregnated with, or otherwise coupled to drugs or other bioactive substances for a variety of purposes, such as promoting tissue ingrowth, reducing thrombosis, reducing the risk of infection, and the like.

In various embodiments, delivery protocols for the filling structures 112 and 212 will utilize the respective delivery catheters 114 and 214 having the respective expandable elements 116 and 216. When using balloons for the expandable elements 116 and 216, the balloons will preferably be substantially or entirely non-compliant, although compliant and combination compliant/non-compliant balloons may also find use. Each expandable element 116 and 216 or other mechanical expansion components of the respective delivery catheter 114 and 214 will initially be disposed within the respective internal lumen 128 and 228 of the respective filling structure 112 and 212, with the respective filling structure 112 and 212 generally being collapsed into a low width or low profile configuration over the corresponding expandable element 116 and 216. Each delivery catheter 114 and 214 may then be introduced intraluminally into a patient, such as into a corresponding iliac artery and upwardly to a region within an aorta to be treated. Each delivery catheter 114 and 214 also includes the respective filling tube 120 and 220 or other components or structures for delivering a filling medium in a fluid form to the respective internal space 122 and 222 of the respective filling structure 112 and 212. Once at the aneurismal site, the internal lumen 128 and 228 of the respective filling structure 112 and 212 can be expanded using the respective expandable element 116 and 216 on the respective delivery catheter 114 and 214. Each filling structure 112 and 212 itself will be filled and expanded by delivering the filling medium via the respective delivery catheter 114 and 214 into the respective internal space 122 and 222 of the corresponding filling structure 112 and 212. Both expansion and filling operations may be performed simultaneously, or can be performed in either order. The filling structures 112 and 212 and/or the expandable elements 116 and 216 may have radiopaque markers to facilitate placement and/or pressure sensors for monitoring filling and inflation pressures during deployment.

Suitable filling materials will be fluid initially to permit delivery through the delivery catheters 114 and 214 and will be curable or otherwise hardenable so that, once in place, the filling structures 112 and 212 can be given a final shape which will remain after the delivery catheters 114 and 214 are removed. In various embodiments, the fillable materials are curable polymers which, after curing, will have a fixed shape. The polymers may be delivered as liquids, gels, foams, slurries, or the like. In some instances, the polymers may be epoxies or other curable two-part systems. In other instances, the polymer may comprise a single material which, when exposed to the vascular environment within the filling structure, changes state over time, typically from zero to ten minutes. The filling material or medium may also include bulking and other agents to modify density, viscosity, mechanical characteristics, or the like, including microspheres, fibers, powders, gasses, radiopaque materials, drugs, and/or the like. Exemplary filling materials include polyurethanes, collagen, polyethylene glycols, microspheres, and the like. In some embodiments, the filling materials or medium includes polyethylene glycol (PEG) or another polymer that may be polymerized in situ.

The filling structures 112 and 212 may be modified in a variety of other ways. For example, external surfaces of the filling structures 112 and 212 may be partially or entirely modified to enhance placement within an aneurismal space, such as by promoting tissue ingrowth or mechanically interlocking with an inner surface of the aneurysm. Such surface modifications include surface roughening, surface stippling, surface flocking, fibers disposed over the surface, foam layers disposed over the surface, rings, and/or the like. It is also possible to provide biologically active substances over all or a portion of the external surfaces of the filling structures 112 and 212, such as thrombogenic substances, tissue growth promotants, biological adhesives, and/or the like. It would further be possible to provide synthetic adhesives, such as polyacrylamides, over the surfaces to enhance adherence. In some instances, it will be desirable to modify all or a portion of internal surfaces of the filling structures 112 and 212. Such surface modifications may comprise surface roughening, rings, stipples, flocking, foam layers, fibers, adhesives, and/or the like. The purpose of such surface modification will usually be to enhance the filling and bonding to the filling material or medium, and to control a minimum wall thickness when each of the filling structures 112 and 212 is filled, particularly after the filling material has been cured.

Figure 3:
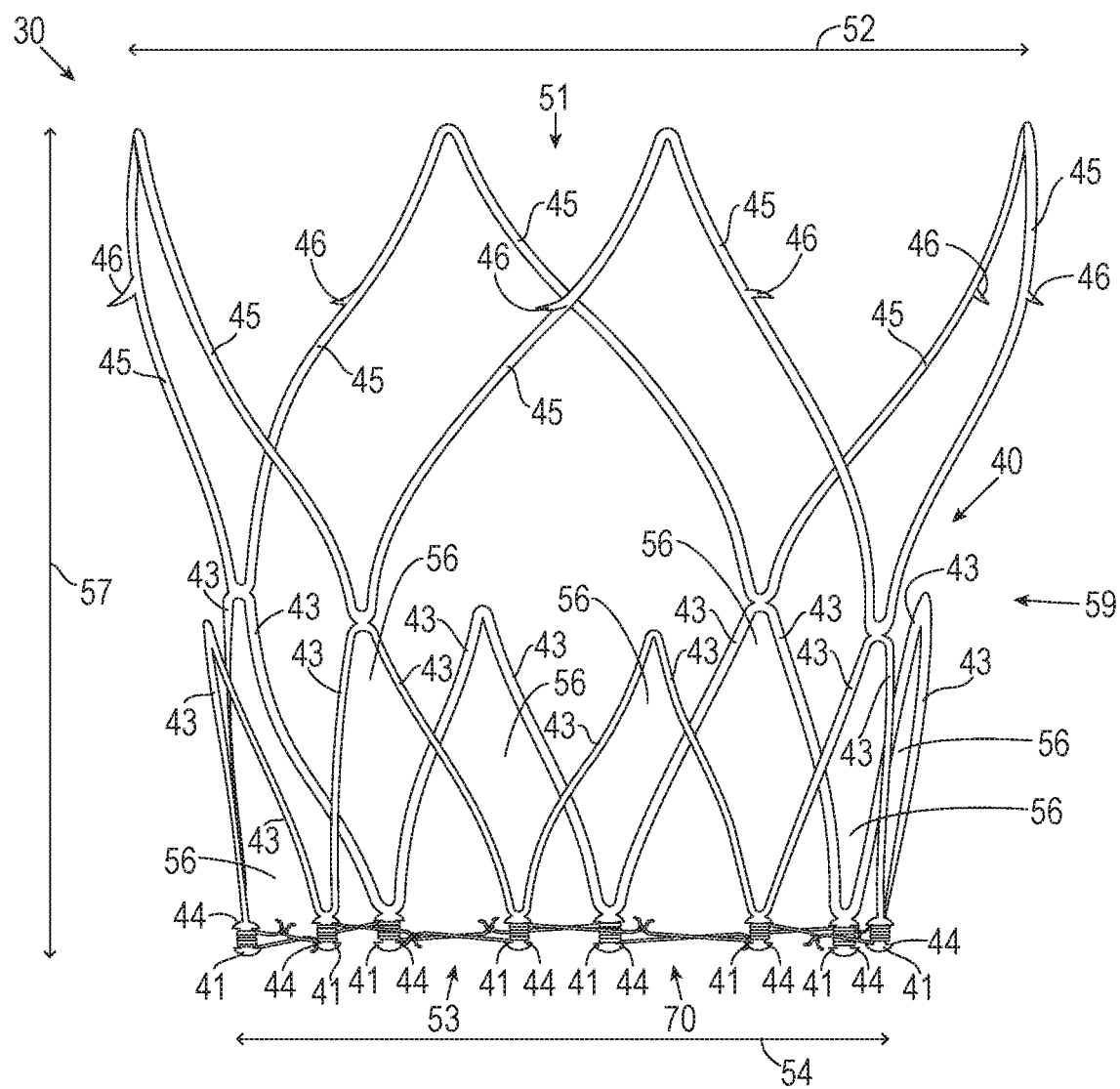
FIG. 3 is an illustration of a side view of an anchor device in accordance with an embodiment.
Figure 4:
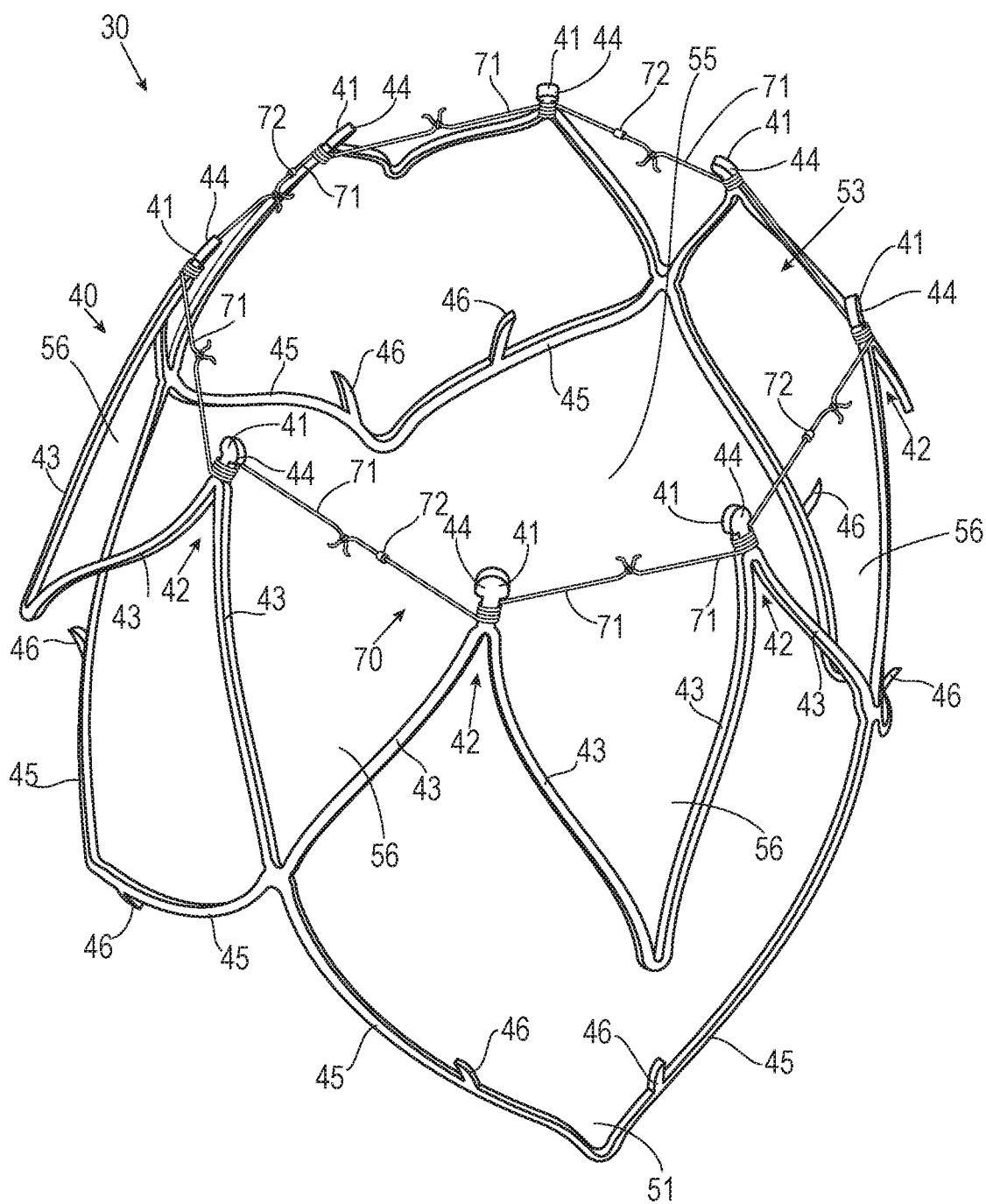
FIG. 4 is a perspective view of the anchor device of FIG. 3 in accordance with an embodiment.

FIG. 3 is an illustration of a side view of the anchor device 30 in accordance with an embodiment. FIG. 4 is a perspective view of the anchor device 30 in accordance with an embodiment looking at a bottom of the anchor device 30. With reference to FIGS. 3 and 4, the anchor device 30 includes the stent 40 and the suture loop 70. The stent 40 includes stent struts 43 on a lower portion of the stent 40, and includes stent struts 45 on an upper portion of the stent 40. The suture loop 70 joins the distal end portions 41 of the stent 40. In various embodiments, the suture loop 70 includes the plurality of suture segments 71 that are tied together to form the suture loop 70. In various embodiments, the plurality of suture segments 71 are arranged in a polygonal arrangement. In some embodiments, the stent 40 includes a plurality of v-shaped stent elements 42 that each have a respective two of the stent struts 43 that meet at a bone shaped apex 44 around which the suture loop 70 is wrapped. In some embodiments, rather than a bone shaped apex 44 there is an eyelet through which the suture loop 70 passes. Also, in some embodiments, the suture loop 70 is wrapped around each of the distal end portions 41 of the stent 40 so as to join the distal end portions 41 of the stent 40.

In various embodiments, the anchor device 30 includes the stent 40 and the stent 40 includes barbs 46 on the stent struts 45 for attachment to a blood vessel, such as a wall of an aorta. In various embodiments, the anchor device 30 further includes radiopaque material 72 positioned on at least a portion of the suture loop 70. In some embodiments, the radiopaque material 72 includes one or more thin-walled metal tubes placed at one or more locations on the suture loop 70 for visibility under an x-ray fluoroscope and includes, for example, a high density metal, such as platinum, gold, tantalum, or the like.

In some embodiments, the stent 40 is expandable to an expanded state such as is shown in FIGS. 3 and 4, and the anchor device 30 is configured such that when the stent 40 is in the expanded state a diameter 52 of a proximal aperture 51 of the stent 40 is greater than a diameter 54 of a distal aperture 53 of the stent 40 that is bounded by the suture loop 70. Also, in some embodiments, the anchor device 30 is configured such that when the stent 40 is in the expanded state the diameter 54 of the distal aperture 53 of the stent 40 is at least 5% smaller than the diameter 52 of the proximal aperture 51 of the stent 40. In some embodiments, the anchor device 30 is configured such that when the stent 40 is in the expanded state the diameter 54 of the distal aperture 53 of the stent 40 is no less than 25% smaller than the diameter 52 of the proximal aperture 51 of the stent 40. There is an area 55 within the stent 40 into which filling structures are insertable. The anchor device 30 has openings 56 that are each bounded by a respective two stent struts 43 and a respective portion of the suture loop 70. There are one or more of the openings 56 in a side 59 of the stent 40. The stent 40 has a length 57 from a proximal end of the stent 40 to a distal end of the stent 40.

Figure 5:
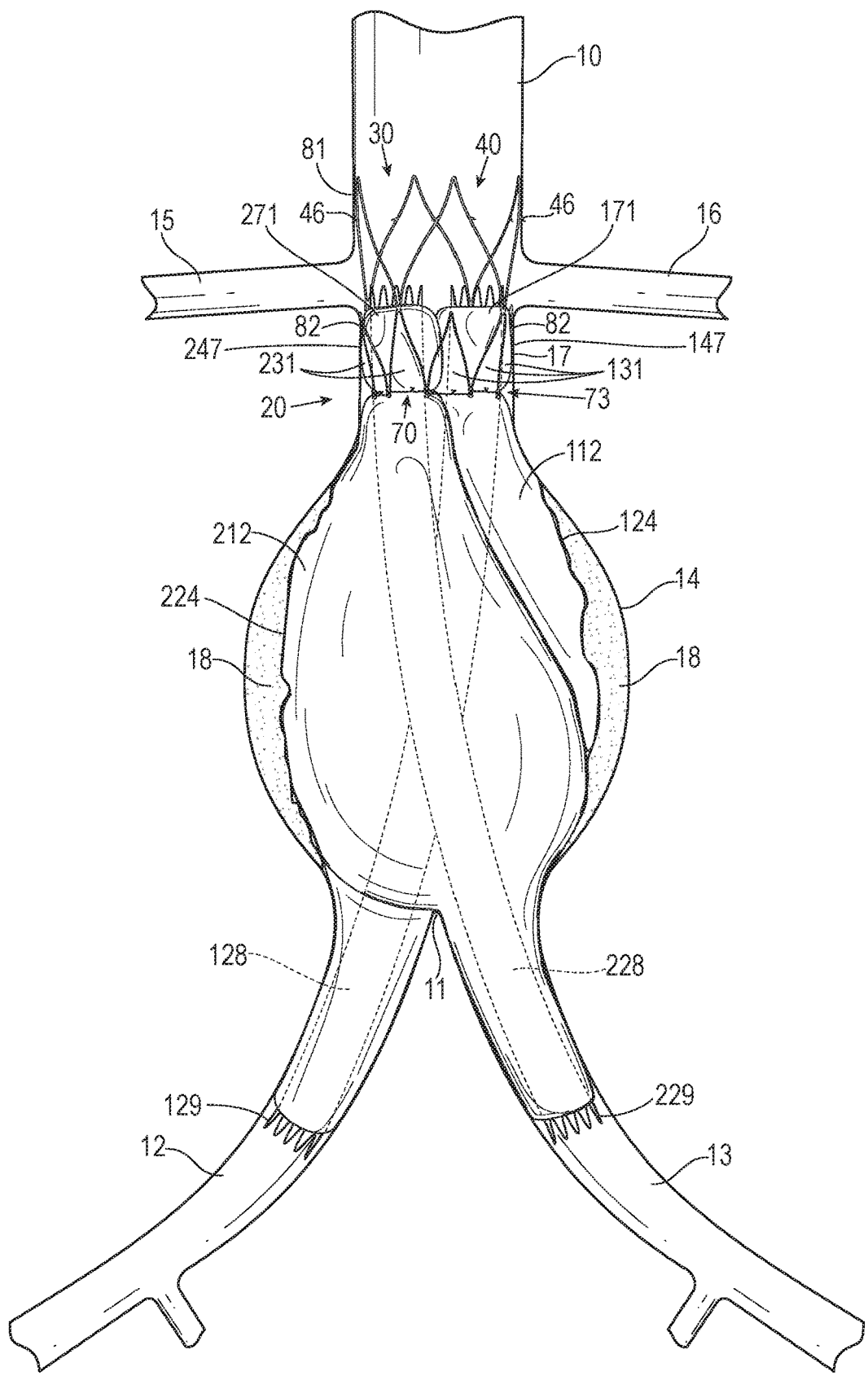
FIG. 5 is an illustration of a system in accordance with an embodiment deployed to repair an aneurysm.
Figure 6:
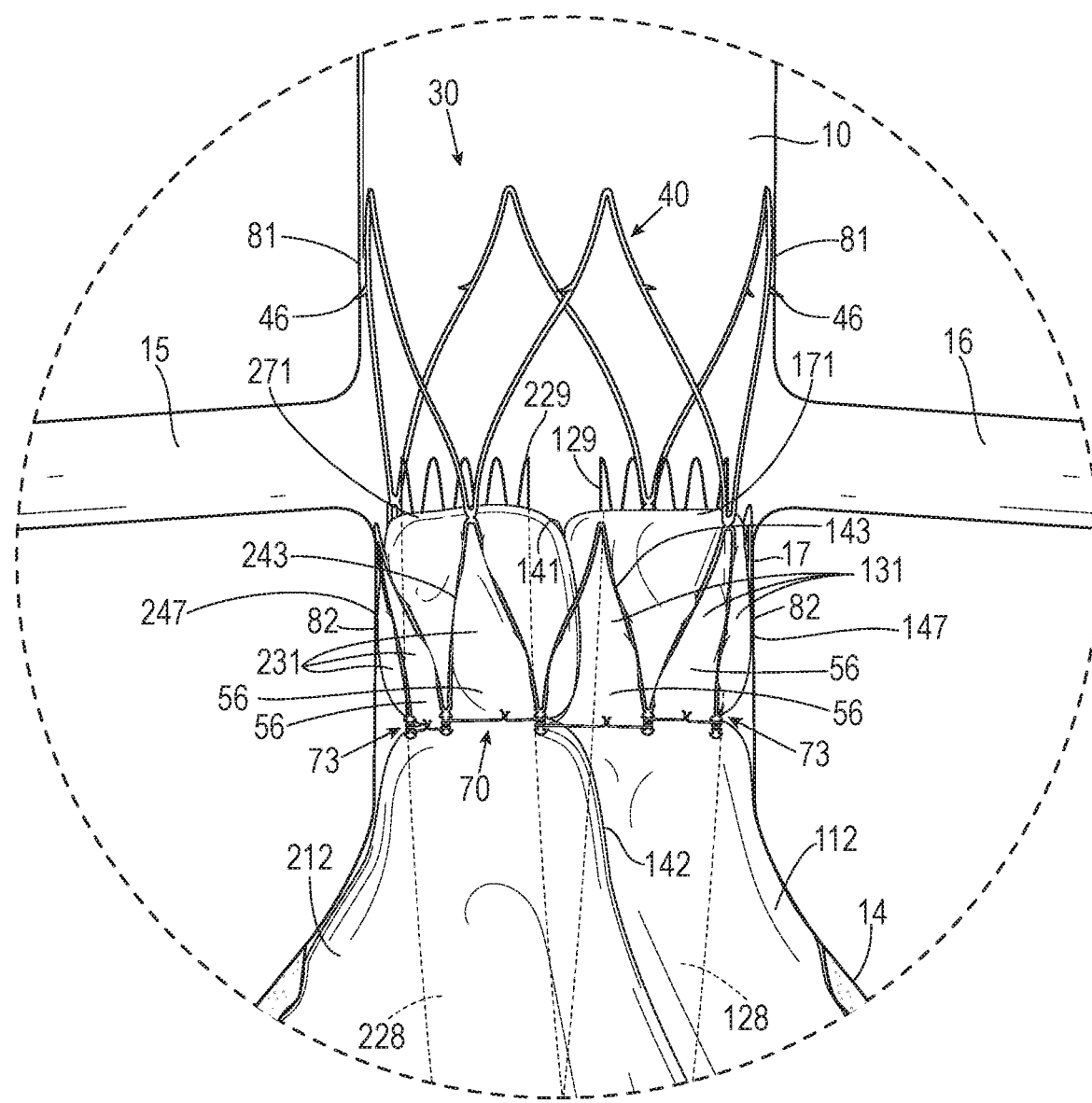
FIG. 6 shows a portion of the system of FIG. 5 including an anchor device, a first filling structure, and a second filling structure in accordance with an embodiment.

FIG. 5 is an illustration of the system 20 in accordance with an embodiment deployed to repair the aneurysm 14 in the aorta 10. FIG. 6 shows a portion of the system 20 of FIG. 5 including the anchor device 30, the filling structure 112, and the filling structure 212 in accordance with an embodiment. In various embodiments, the stent 40 is expandable to an expanded state as in FIGS. 5 and 6, and the filling structure 112 and the filling structure 212 are at least partially insertable through the suture loop 70 to an area within the stent 40 when the stent 40 is in the expanded state. In some embodiments, the anchor device 30 has a size such that one or more portions 131 of the filling structure 112 and one or more portions 231 of the filling structure 212 protrude through the openings 56 in the anchor device 30 when the filling structure 112 and the filling structure 212 have been at least partially inserted through the suture loop 70 and have been filled. With reference to FIGS. 3, 4, 5, and 6, in some embodiments, the openings 56 in the anchor device 30 are bounded by the stent struts 43 of the stent 40 and the suture loop 70. Also, in some embodiments, the filling structure 112 and the filling structure 212 are sealable against each other as shown by the seal areas 141 and 142 and are lockable onto, fixable to, or joinable to the anchor device 30 when filled as shown by the locking areas 143 and 243.

In various embodiments, the stent 40 has a sufficient length 57 such that the filling structure 112 and the filling structure 212 are deployable when extending at least 20 mm within the stent 40. In some embodiments, the anchor device 30 includes the barbs 46 that are attachable to a wall 81 of the aorta 10 above the renal arteries 15 and 16, and the anchor device 30 has a size such that the one or more portions 131 of the filling structure 112 and the one or more portions 231 of the filling structure 212 protrude through the openings 56 in the anchor device 30 to contact a wall 82 of the aorta 10 below the renal arteries 15 and 16 when the barbs 46 have been attached to the aorta 10 above the renal arteries 15 and 16 and the filling structure 112 and the filling structure 212 have been at least partially inserted through the suture loop 70 and have been filled.

In various embodiments, the suture loop 70 is configured to at least partially constrain the filling structure 112 and the filling structure 212 when the filling structure 112 and the filling structure 212 have been at least partially inserted through the suture loop 70 and have been filled as shown by the constraining area 73. In some embodiments, the filling structure 112 is deployable to provide the internal lumen 128 for blood flow from the aorta 10 to the iliac artery 12, and the filling structure 212 is deployable to provide the internal lumen 228 for blood flow from the aorta 10 to the iliac artery 13. Also, in some embodiments, the stent 40 includes the plurality of stent struts 43 and the plurality of stent struts 45 that are each made of, for example, a nickel-titanium alloy, and the suture loop 70 is made of, for example, thread.

In various embodiments, when the filling structure 112 has been filled, the one or more portions 131 of the filling structure 112 protrude through the anchor device 30 to form a seal against the wall 82 of the aorta 10 below the renal arteries 15 and 16 as shown by the example seal area 147. Also, in various embodiments when the filling structure 212 has been filled, the one or more portions 231 of the filling structure 212 protrude through the anchor device 30 to form a seal against the wall 82 of the aorta 10 below the renal arteries 15 and 16 as shown by the example seal area 247. In various embodiments, a proximal end 171 of the filling structure 112 remains below a top of the renal arteries 15 and 16 after the filling structure 112 has been filled. Also, in various embodiments, a proximal end 271 of the filling structure 212 remains below a top of the renal arteries 15 and 16 after the filling structure 212 has been filled.

In some embodiments, the suture loop 70 is elastic to allow for an additional expansion of the stent 40 when the filling structure 112 and the filling structure 212 are filled. In various embodiments, the anchor device 30 includes a mechanical interlock or the like to not expand beyond a certain point. In various embodiments, the filling structure 112 and the filling structure 212 form a seal against each other both within the stent 40 as shown by the seal area 141 and outside of the stent 40 as shown by the seal area 142. In various embodiments, the filling structure 112 is filled to form a seal against the wall 82 of the aorta 10 below the renal arteries 15 and 16 as shown by the seal area 147 and to form a seal against the filling structure 212 as shown by the seal area 141. In various embodiments, the filling structure 212 is filled to form a seal against the wall 82 of the aorta 10 below the renal arteries 15 and 16 as shown by the seal area 247 and to form a seal against the filling structure 112 as shown by the seal area 141.

In various embodiments, the filling structure 112 and the filling structure 212 are filled to form a seal with each other above the suture loop 70 as shown by the seal area 141 and to form a seal with each other below the suture loop 70 as shown by the seal area 142. In various embodiments, the filling structure 112 and the filling structure 212 are filled to form a seal with a wall of the aorta 10 both above the suture loop 70 and below the suture loop 70. In some embodiments, the filling structure 112 and the filling structure 212 are pre-shaped to have different expanding portions that are shaped differently for expansion above the suture loop 70 and below the suture loop 70.

While the stent 40 has been depicted as an example with a number of stent struts 43, stent struts 45, and barbs 46, it should be understood that any desirable number of stent struts 43, stent struts 45, and barbs 46 can be used in various embodiments. For example, the number of barbs 46 in various embodiments may be 1, 2, 3, 4, 5, 6, 7, 8, 9, 10, or any other number of desired barbs 46. The length 57 of the stent 40 can vary for different embodiments of the stent 40 and can be chosen, for example, based on the anatomy of a patient. Also, the diameter 52 of the proximal aperture 51 of the stent 40 and the diameter 54 of the distal aperture 53 of the stent 40 can be different for different embodiments of the stent 40 and a particular size of stent can be chosen, for example, based on the anatomy of a patient. The lengths of the filling structure 112 and the filling structure 212 could also be chosen, for example, based on the anatomy of a patient.

FIG. 7 is a flowchart of a method in accordance with an embodiment for repairing one or more blood vessels. The method of FIG. 7 can be used to deploy the system 20 of FIG. 2 into one or more blood vessels, such as the aorta 10 and iliac arteries 12 and 13 of FIG. 1. FIGS. 8, 9, 10, 11, 12, and 13 show various steps of the deployment based on the method of FIG. 7 to result in the deployed state of the system 20 shown in FIG. 5.

Figure 8:
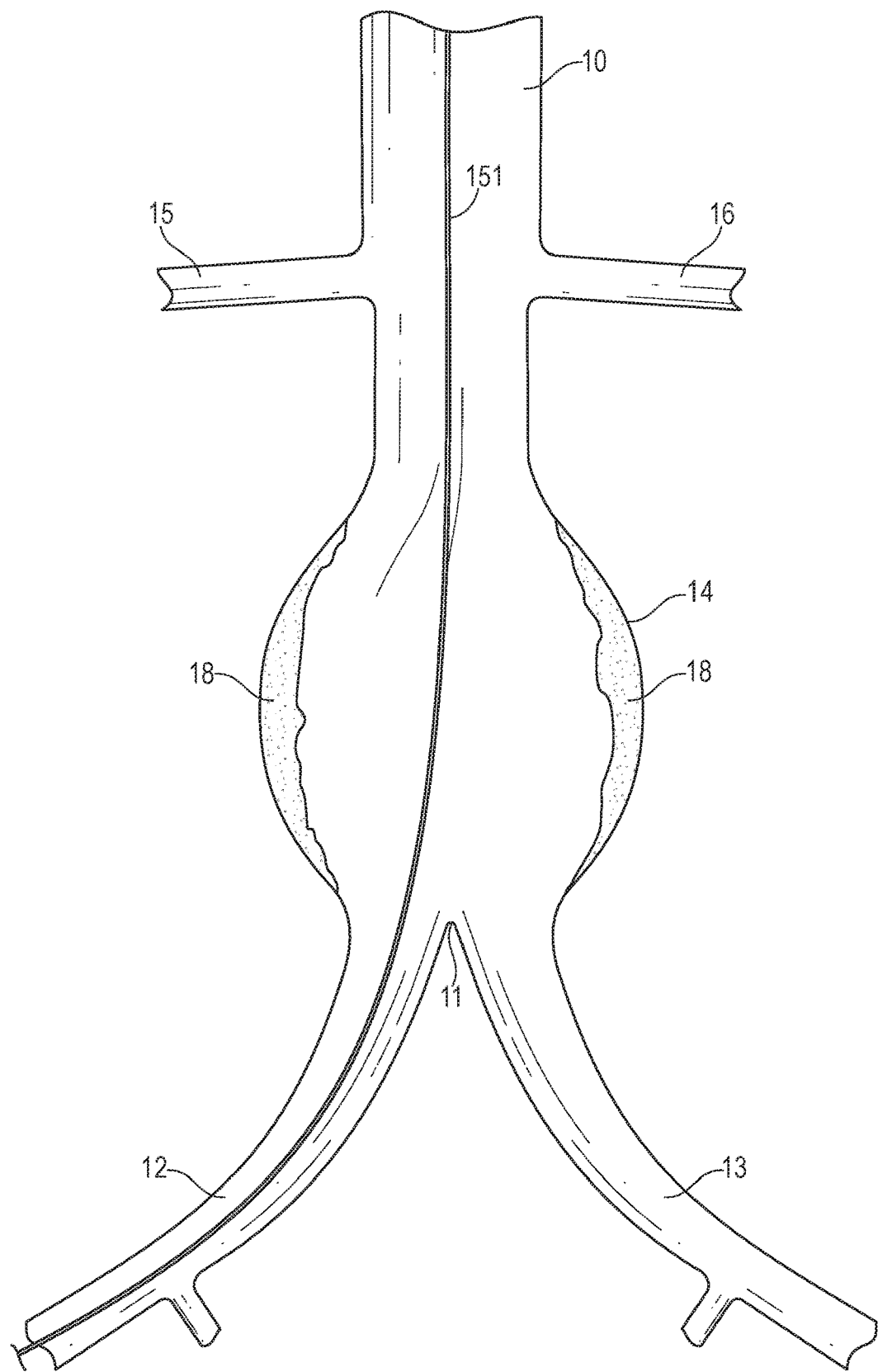
FIG. 8 is an illustration of a first guidewire inserted through a first iliac artery into an aorta.
Figure 9:
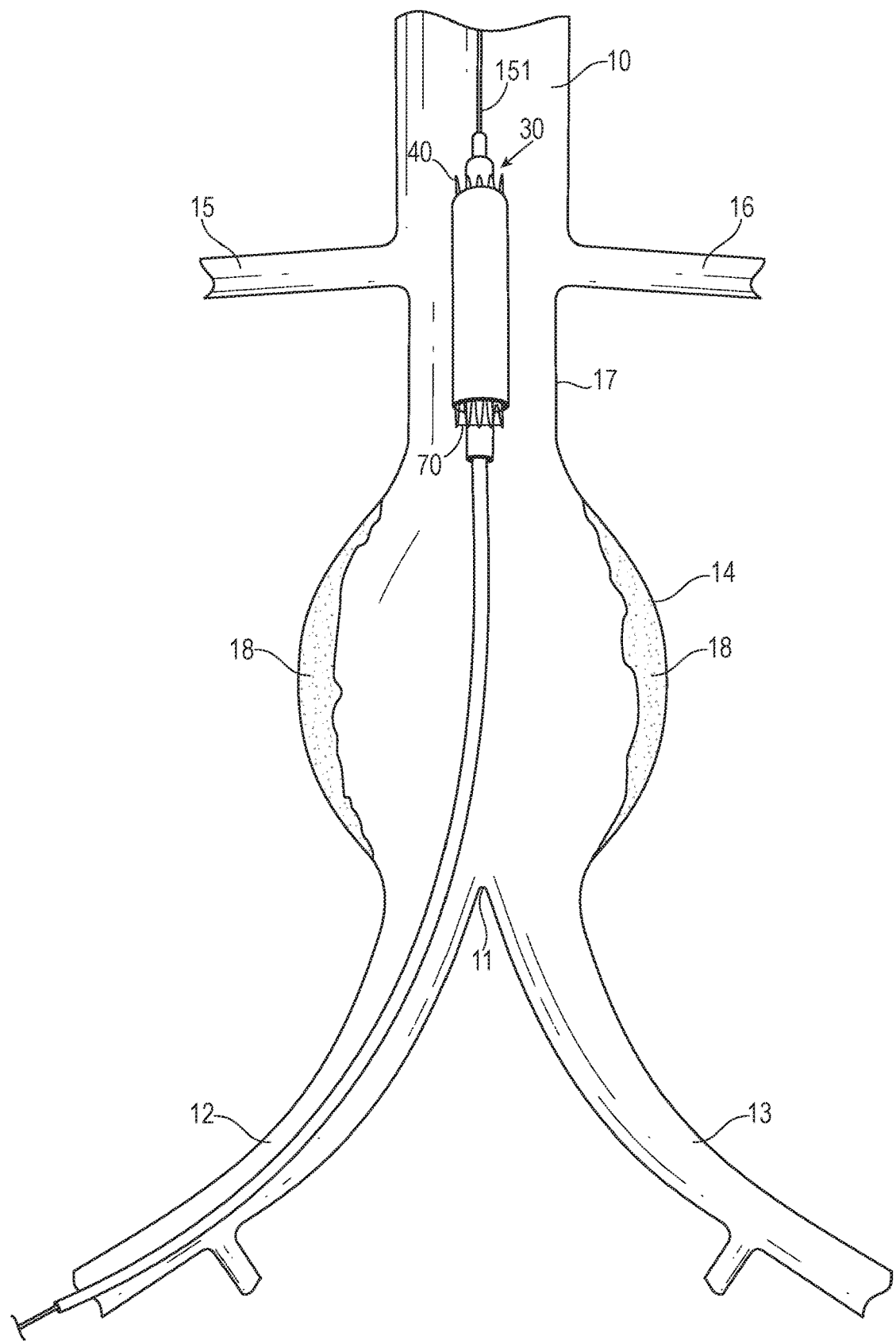
FIG. 9 is an illustration of inserting an anchor device in accordance with an embodiment into the aorta using the first guidewire of FIG. 8.
Figure 10:
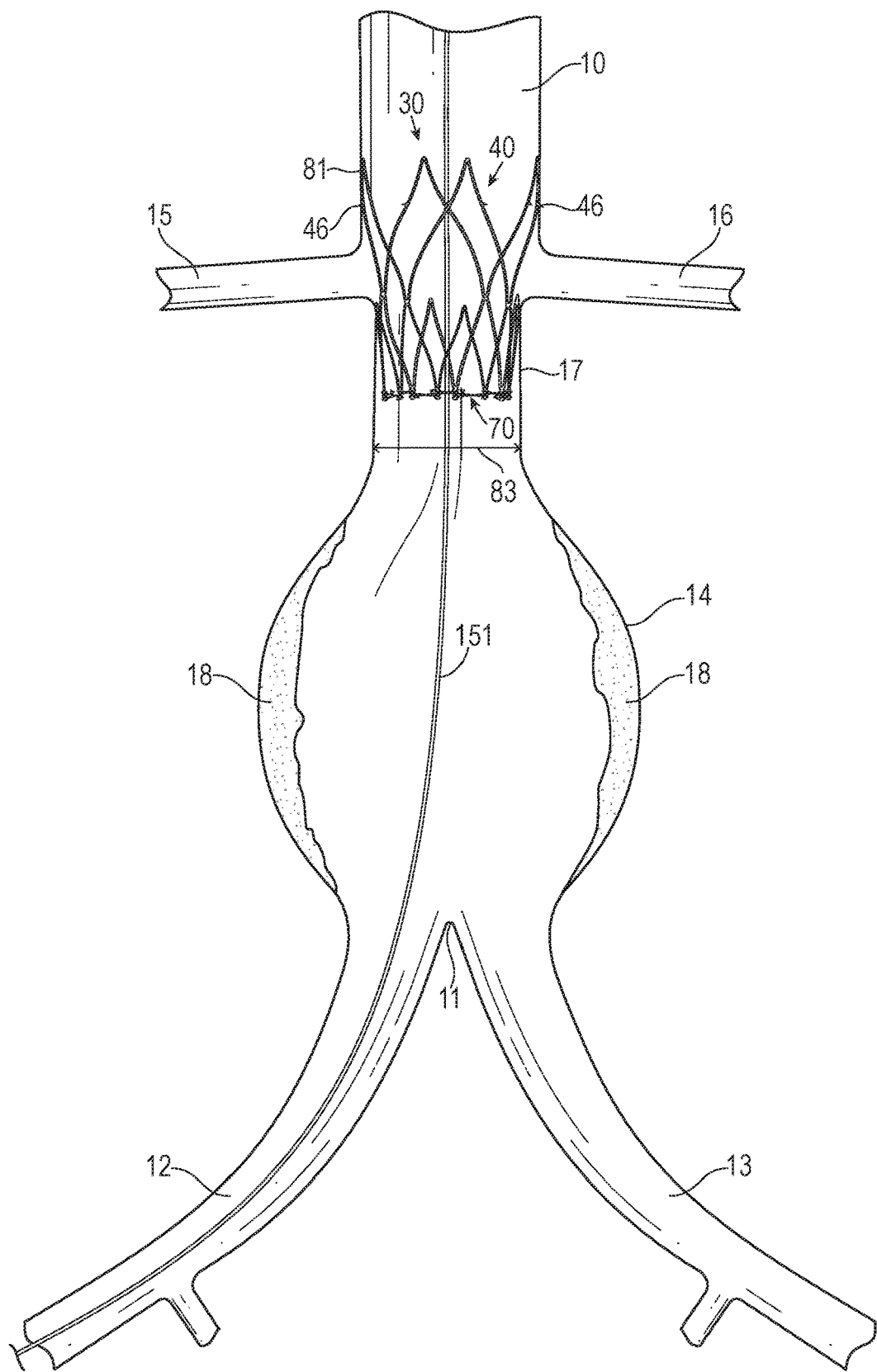
FIG. 10 is an illustration of deployment of the anchor device in accordance with an embodiment in the aorta.

With reference to FIG. 7, in step 400 an anchor device is chosen from among a plurality of anchor devices of different sizes based on a diameter of a proximal neck region of an aneurysm in a patient. For example, with reference to FIG. 1, the diameter 83 of the proximal neck region 17 of the aneurysm 14 in the aorta 10 can be measured for a patient and then an anchor device can be chosen from among a plurality of anchor devices of different sizes based on the diameter 83 of the proximal neck region 17 of the aneurysm 14. With reference to FIG. 7, in step 401 an anchor device is deployed that has a stent and a suture loop that joins distal end portions of the stent. Examples of steps in such deployment are shown in FIGS. 8, 9, and 10. With reference to FIG. 8, a guidewire 151 is inserted through an incision in a patient's groin and is extended through the iliac artery 12 and through the aorta 10 past the renal arteries 15 and 16. With reference to FIG. 9, a catheter that holds the anchor device 30 in a compressed state is advanced over the guidewire 151 through the iliac artery 12 to the location in the aorta 10 for deployment. The anchor device 30 includes the stent 40 and the suture loop 70 and can be held in a compressed state, for example, by a sheath or the like. With reference to FIG. 10, the anchor device 30 expands within the aorta 10 to an expanded state. Thus, in various embodiments, the anchor device 30 is deployed using the guidewire 151 that passes through the iliac artery 12.

Figure 11:
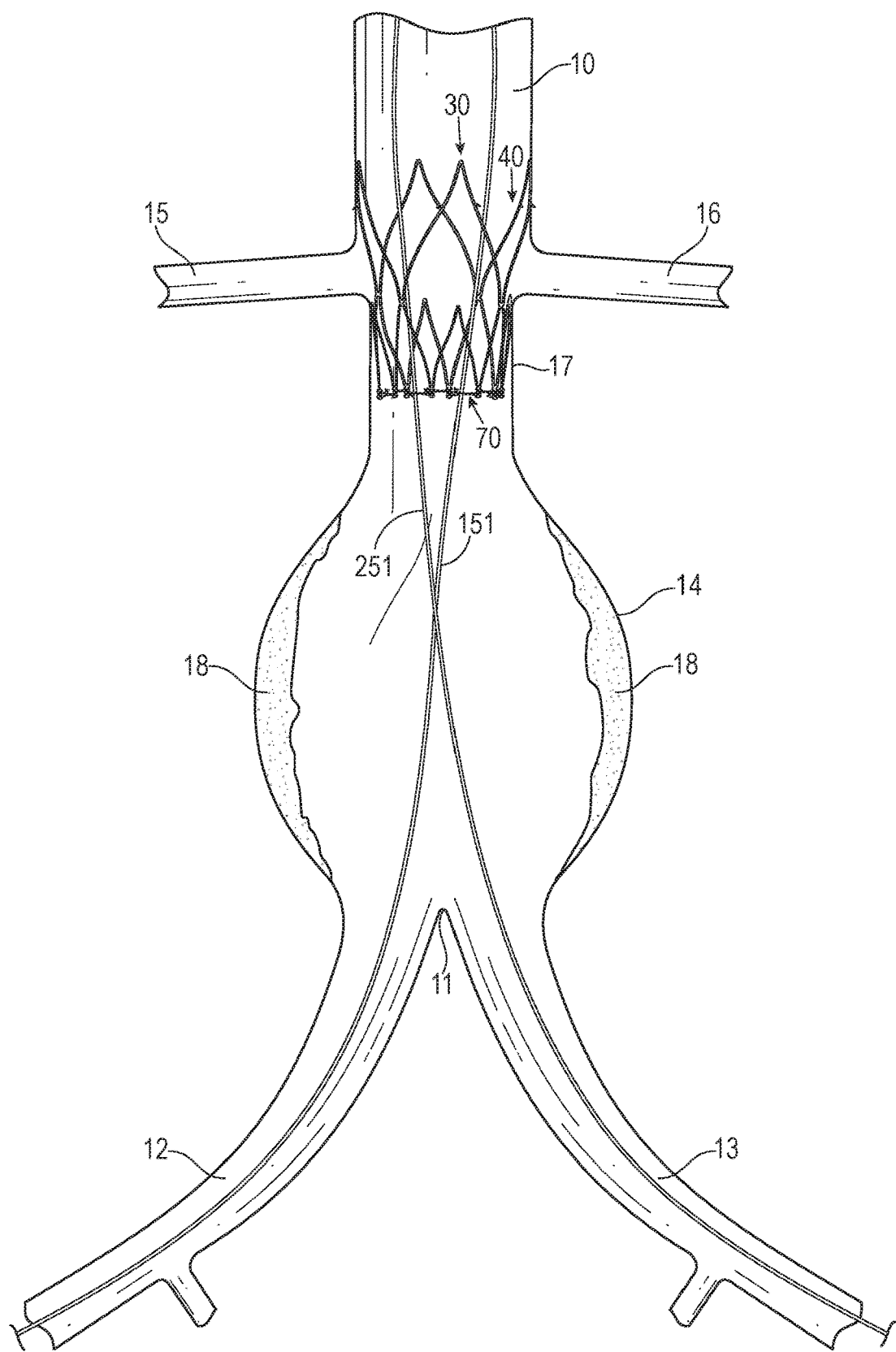
FIG. 11 is an illustration of the first guidewire passing through the anchor device in accordance with an embodiment, and also shows a second guidewire that has been inserted through a second iliac artery and through the anchor device.

With reference to FIGS. 3, 4, and 10, in various embodiments, the anchor device 30 is deployed at least partially in the proximal neck region 17 of the aneurysm 14 and, after deployment of the anchor device 30, the distal aperture 53 of the stent 40 that is bounded by the suture loop 70 has the diameter 54 that is at least 5% smaller than the diameter 83 of the proximal neck region 17 of the aneurysm 14. With reference to FIGS. 7 and 10, in various embodiments the deploying of the anchor device 30 includes the step 402 of fixing the barbs 46 to the wall 81 of the aorta 10 above the renal arteries 15 and 16. In some embodiments, after deployment of the anchor device 30, the stent 40 extends down in the aorta 10 past the renal arteries 15 and 16 and has a length below the renal arteries 15 and 16 that is at least 20 mm. The guidewire 151 that passes through the iliac artery 12 can remain through the anchor device 30 in the aorta 10 after the anchor device 30 has been deployed in order to allow for further deployment of a filling structure. Another guidewire can then be inserted through the other iliac artery 13 for deploying another filling structure. With reference to FIG. 11, a guidewire 251 is inserted through another incision in the patient's groin and is extended through the iliac artery 13 and through the aorta 10 past the renal arteries 15 and 16. The guidewire 251 passes through the stent 40 of the anchor device 30. In various embodiments, the guidewire 251 crosses the guidewire 151 within the aneurysm 14.

Figure 12:
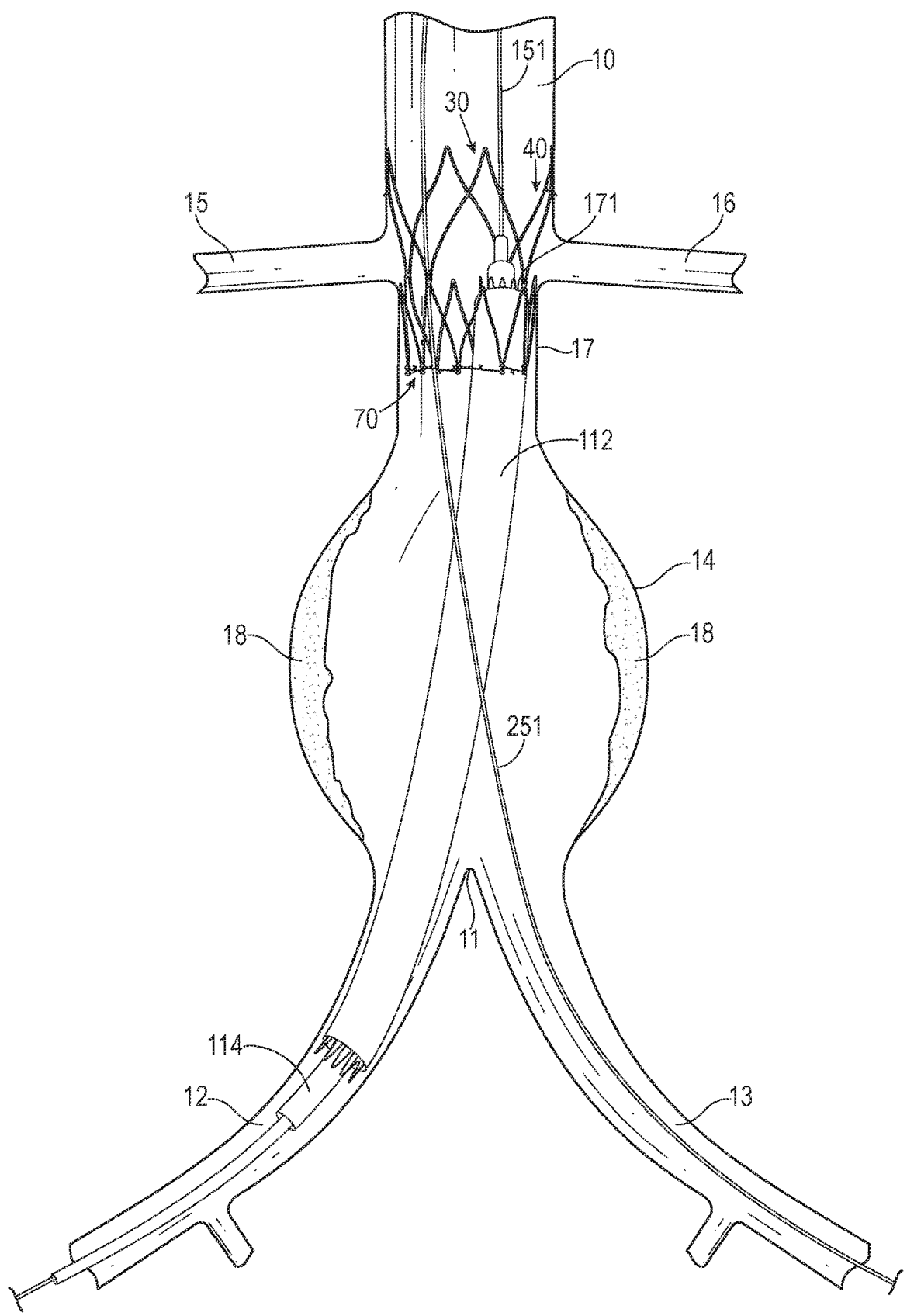
FIG. 12 is an illustration of inserting a first catheter holding a first filling structure at least partially into the anchor device using the first guidewire in accordance with an embodiment.

With reference again to FIG. 7, in step 403, a first filling structure is inserted at least partially through the suture loop. For example, with reference to FIG. 12, the delivery catheter 114 holding the filling structure 112 is advanced over the guidewire 151 through the iliac artery 12 and at least partially through the suture loop 70 into an area within the stent 40 of the anchor device 30 in the aorta 10. Thus, in various embodiments, the filling structure 112 is inserted for deployment using the same guidewire 151 that was used to deploy the anchor device 30 and that passes through the iliac artery 12. With reference to FIGS. 4, 7, and 12, in some embodiments the inserting of the filling structure 112 includes the step 404 of viewing the radiopaque material 72 on at least a portion of the suture loop 70 to aid the insertion of the filling structure 112 at least partially through the suture loop 70. In various embodiments, the viewing is performed using an x-ray fluoroscope or the like. In some embodiments, the inserting of the filling structure 112 includes the step 405 of inserting the proximal end 171 of the filling structure 112 at least 20 mm past the suture loop 70 and keeping the filling structure 112 entirely below the renal arteries 15 and 16. The filling structure 112 passes through the suture loop 70 by passing through an area surrounded by the suture loop 70, such that at least a portion of the filling structure 112 is surrounded by the suture loop 70.

In step 406, a second filling structure is inserted at least partially through the suture loop. For example, with reference to FIG. 13, the delivery catheter 214 holding the filling structure 212 is advanced over the guidewire 251 through the iliac artery 13 and at least partially through the suture loop 70 into an area within the stent 40 of the anchor device 30 in the aorta 10. Thus, in various embodiments, the filling structure 212 is inserted for deployment through the iliac artery 13 using the guidewire 251 that is a separate guidewire from the guidewire 151 that passes through the iliac artery 12 and that was used to insert the anchor device 30 and filling structure 112.

Figure 13:
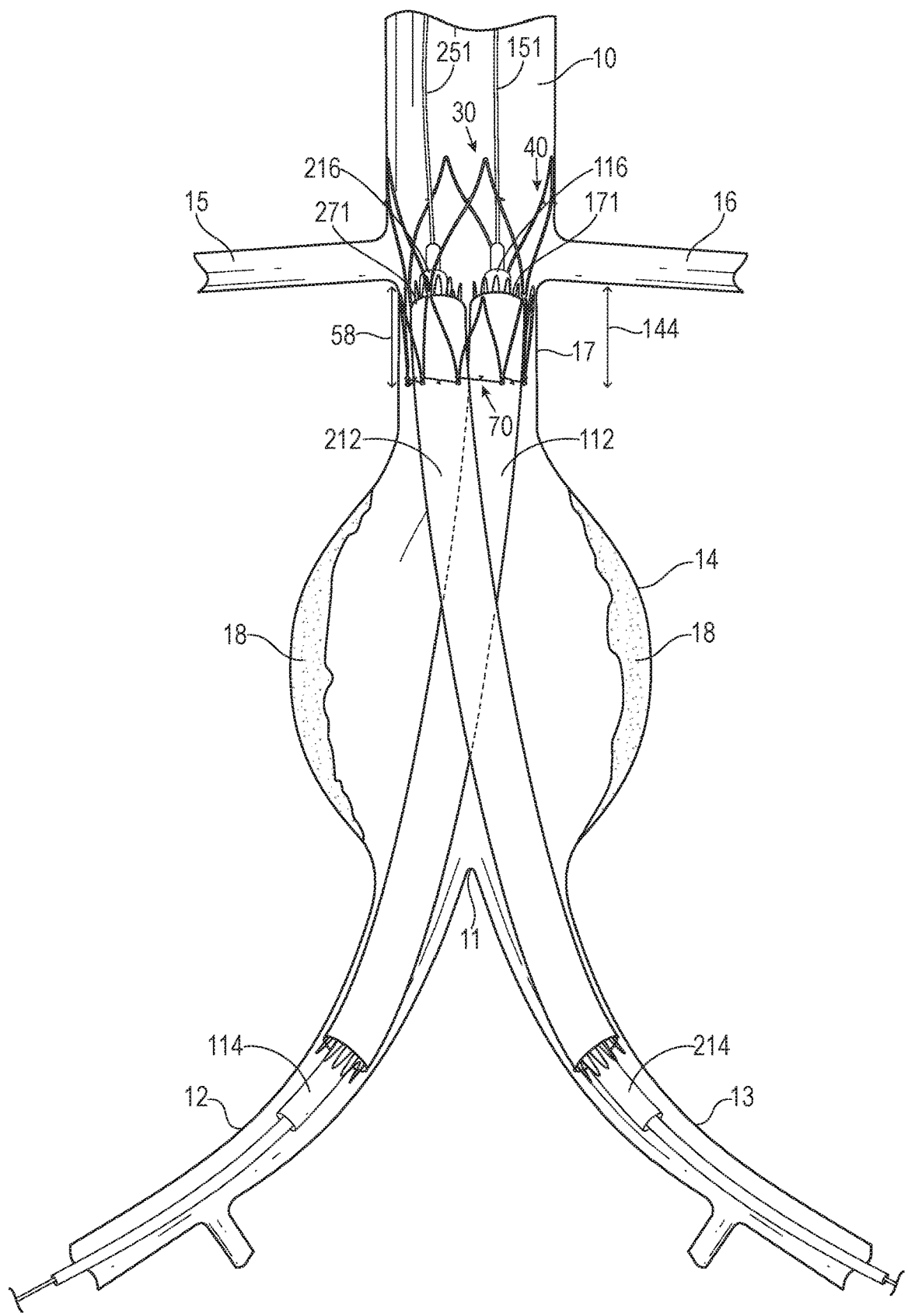
FIG. 13 is an illustration of inserting a second catheter holding a second filling structure at least partially into the anchor device using the second guidewire in accordance with an embodiment.

With reference to FIGS. 4, 7, and 13, in some embodiments the inserting of the filling structure 212 includes the step 407 of viewing the radiopaque material 72 on at least a portion of the suture loop 70 to aid the insertion of the filling structure 212 at least partially through the suture loop 70. In various embodiments, the viewing is performed using an x-ray fluoroscope or the like. In some embodiments, the inserting of the filling structure 212 includes the step 408 of inserting the proximal end 271 of the filling structure 212 at least 20 mm past the suture loop 70 and keeping the filling structure 212 entirely below the renal arteries 15 and 16. The filling structure 212 passes through the suture loop 70 by passing through an area surrounded by the suture loop 70, such that at least a portion of the filling structure 212 is surrounded by the suture loop 70. In various embodiments, the filling structure 112 and the filling structure 212 extend a length 144 within the stent 40. Also, in various embodiments, a length 58 of the stent 40 below the renal arteries 15 and 16 is sufficient such that the filling structure 112 and the filling structure 212 can extend at least 20 mm above the suture loop 70 while still remaining entirely below the renal arteries 15 and 16.

In step 409, the first filling structure is filled to cause one or more portions of the first filling structure to protrude through one or more openings bounded by one or more stent struts of the stent and at least a portion of the suture loop. For example, FIG. 5 shows the filling structure 112 after it has been filled with a filling material or medium. With reference to FIGS. 3, 4, and 5, the filling structure 112 is filled to cause the one or more portions 131 of the filling structure 112 to protrude through the one or more openings 56 bounded by a respective one or more of the stent struts 43 of the stent 40 and at least a respective portion of the suture loop 70. With reference to FIGS. 3, 4, 5, 6, and 7, in various embodiments filling the filling structure 112 includes the step 410 of filling the filling structure 112 with a polymer that sets after the one or more portions 131 of the filling structure 112 have protruded through the one or more openings 56 so as to lock the filling structure 112 to the anchor device 30 as shown by the lock area 143. In various embodiments, the filling structure 112 is filled with a polymer, and the filling structure 112 is at least partially constrained by the suture loop 70 when the filling structure 112 is filled with the polymer as shown by the constraining area 73.

In step 411, the second filling structure is filled to cause one or more portions of the second filling structure to protrude through a corresponding one or more openings in a side of the stent. For example, the filling structure 212 is filled to cause the one or more portions 231 of the filling structure 212 to protrude through the corresponding one or more openings 56 in a side of the stent 40 that are bounded by portions of the suture loop 70. In various embodiments, the filling of the filling structure 212 includes the step 412 of filling the filling structure 212 to cause the filling structure 212 to form a seal with the filling structure 112 both inside of the stent 40 and outside of the stent 40, which is shown by the two seal areas 141 and 142. In various embodiments, at least a portion of the filling structure 212 is constrained by the suture loop 70 when the filling structure 212 has been filled. In various embodiments, the one or more portions 131 of the filling structure 112 and the one or more portions 231 of the filling structure 212 contact the wall 82 of the aorta 10 to form a seal against the wall 82, which is shown by the seal areas 147 and 247. In some embodiments, the steps 403 and 406 are performed at a same time as each other. Also, in some embodiments, the steps 409 and 411 are performed at a same time as each other. In some embodiments, the steps 403, 406, 409, and 411 are performed sequentially.

In various embodiments, the filling structures 112 and 212 treat the aneurysm 14 by each providing the respective lumen 128 and 228 across the aneurysm 14. By "across" the aneurysm 14, it is meant generally that in various embodiments the filling structures 112 and 212 extend axially from a respective anatomical location which has been identified by imaging or otherwise as above the beginning of the aneurysm 14 to a respective location that is below where it has been established that the aneurysm 14 ends. In various embodiments, the filling structures 112 and 212 are positioned across the aneurysm 14 and the respective outer walls 124 and 224 of each filling structure 112 and 212 conform to an inside surface of the aneurysm 14 as well as to each other, thus providing a pair of tubular internal lumens 128 and 228 for blood flow from the aorta 10 to each of the iliac arteries 12 and 13, respectively. In various embodiments, the iliac artery 12 is an ipsilateral iliac artery, and the iliac artery 13 is a contralateral iliac artery.

Figure 14:
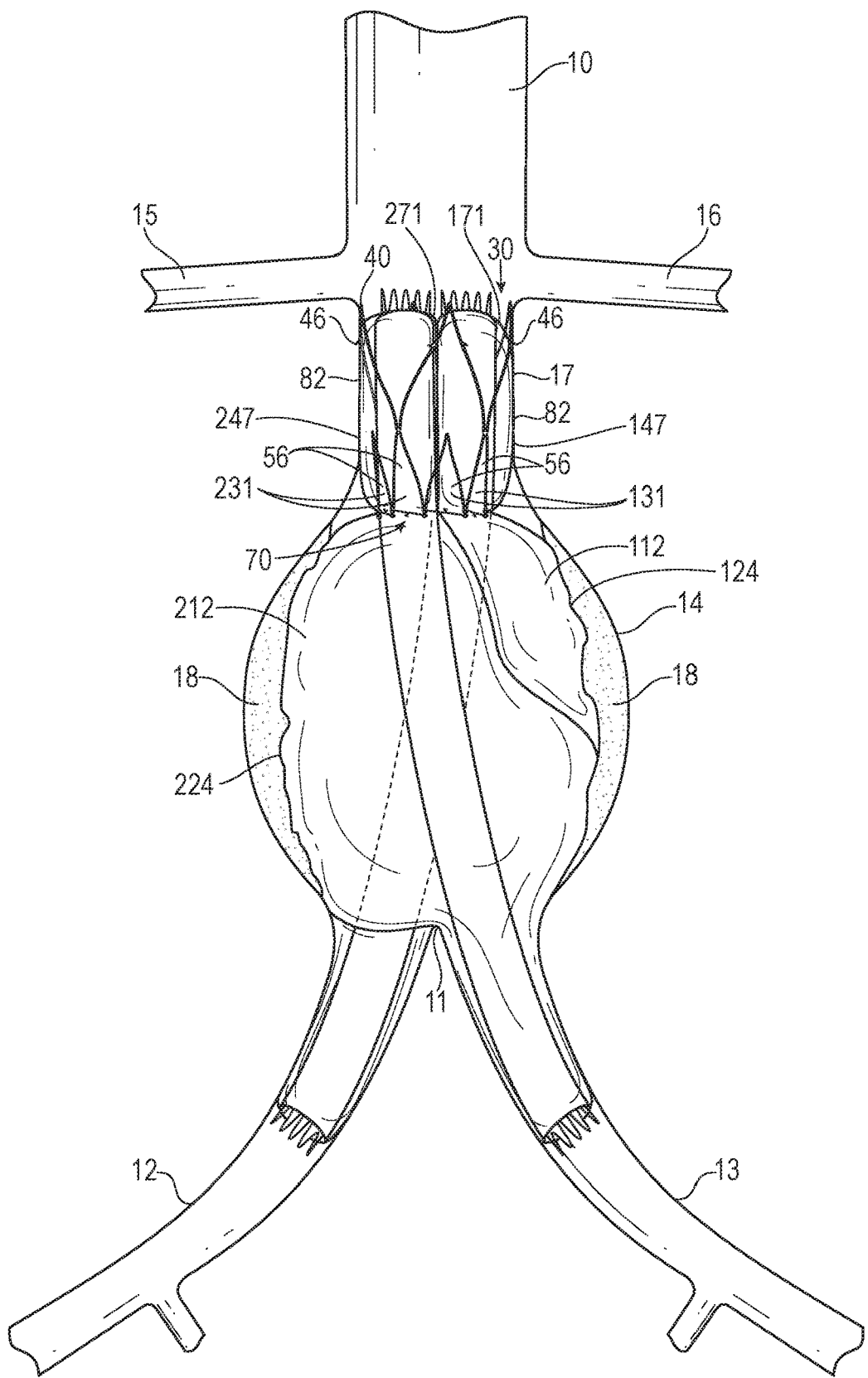
FIG. 14 is an illustration of a system in accordance with an embodiment deployed to repair one or more blood vessels with an anchor device positioned below renal arteries.

FIG. 14 is an illustration of the system 20 of FIG. 2 deployed to repair the aorta 10 with the anchor device 30 positioned below the renal arteries 15 and 16. The deployment in FIG. 14 is similar to the deployment of FIG. 5, but in FIG. 14 the anchor device 30 is deployed entirely below the renal arties 15 and 16. In FIG. 14, the filling structure 112 and the filling structure 212 extend up to a top of the anchor device 30 such that the proximal end 171 of the filling structure 112 and the proximal end 271 of the filling structure 212 extend to at or near a top of the stent 40. The one or more portions 131 of the filling structure 112 protrude through one or more of the openings 56 bounded by respective portions of the suture loop 70 to contact the wall 82 of the aorta 10 below the renal arteries 15 and 16 and form a seal with the wall 82 as shown by the seal area 147. The one or more portions 231 of the filling structure 212 protrude through one or more of the openings 56 bounded by respective portions of the suture loop 70 to contact the wall 82 of the aorta 10 below the renal arteries 15 and 16 and form a seal with the wall 82 as shown by the seal area 247. In some embodiments, the barbs 46 are fixed to the wall 82 of the aorta 10 below the renal arteries 15 and 16.

The embodiments disclosed herein are to be considered in all respects as illustrative, and not restrictive of the invention. The present invention is in no way limited to the embodiments described above. Various modifications and changes may be made to the embodiments without departing from the spirit and scope of the invention. Various modifications and changes that come within the meaning and range of equivalency of the claims are intended to be within the scope of the invention.

What is claimed is:

1. A system for deployment in a blood vessel, the system comprising:
   an anchor device comprising
      a stent; and
      a suture loop that joins distal end portions of the stent; and
   a filling structure;
      wherein the stent is expandable to an expanded state,
      wherein the filling structure is at least partially insertable through the suture loop to an area within the stent when the stent is in the expanded state; and
      wherein the anchor device has a size such that at least a portion of the filling structure protrudes through openings in the anchor device when the filling structure has been at least partially inserted through the suture loop and has been filled.

2. The system of claim 1,
   wherein the suture loop comprises a plurality of suture segments tied together, each suture segment extending from an apex of the stent to an adjacent apex of the stent.

3. The system of claim 1,
   wherein the stent comprises a plurality of v-shaped stent elements that each have two stent struts that meet at a dog-bone shaped apex around which the suture loop is wrapped.

4. The system of claim 1,
   wherein the suture loop is wrapped around each of the distal end portions of the stent so as to join the distal end portions of the stent.

5. The system of claim 1,
   wherein the anchor device further comprises radiopaque material positioned on at least a portion of the suture loop.

6. The system of claim 1,
   wherein the stent is expandable to an expanded state; and
   wherein the anchor device is configured such that when the stent is in the expanded state a diameter of a proximal aperture of the stent is greater than a diameter of a distal aperture of the stent that is bounded by the suture loop.

7. The system of claim 6,
   wherein the anchor device is configured such that when the stent is in the expanded state the diameter of the distal aperture of the stent is at least 5% smaller than the diameter of the proximal aperture of the stent.

8. The system of claim 7,
wherein the anchor device is configured such that when the stent is in the expanded state the diameter of the distal aperture of the stent is no less than 25% smaller than the diameter of the proximal aperture of the stent.

9. The system of claim 1,
wherein the openings in the anchor device are bounded by stent struts of the stent and the suture loop.

10. The system of claim 1,
comprising a first filling structure and a second filling structure, wherein the first filling structure and the second filling structure are sealable against each other and are lockable onto the anchor device when filled.

11. The system of claim 10,
wherein the suture loop is configured to at least partially constrain the first filling structure and the second filling structure when the first filling structure and the second filling structure have been at least partially inserted through the suture loop and have been filled.

12. A method for repairing one or more blood vessels, the method comprising:
deploying an anchor device that comprises a stent and a suture loop that joins distal end portions of the stent;
inserting a first filling structure at least partially through the suture loop; and
filling the first filling structure to cause one or more portions of the first filling structure to protrude through one or more openings bounded by one or more stent struts of the stent and at least a portion of the suture loop.

13. The method of claim 12, further comprising:
inserting a second filling structure at least partially through the suture loop; and
filling the second filling structure to cause one or more portions of the second filling structure to protrude through a corresponding one or more openings in a side of the stent.

14. The method of claim 13,
wherein the one or more portions of the first filling structure and the one or more portions of the second filling structure contact a wall of a blood vessel of the one or more blood vessels to form a seal against the wall.

15. The method of claim 13,
wherein the anchor device further comprises radiopaque material on at least a portion of the suture loop; and
wherein the method further comprises viewing the radiopaque material to aid the insertion of the first filling structure at least partially through the suture loop and to aid the insertion of the second filling structure at least partially through the suture loop.

16. The method of claim 12,
wherein the anchor device is deployed at least partially in a proximal neck region of an aneurysm; and
wherein, after deployment of the anchor device, a distal aperture of the stent that is bounded by the suture loop has a diameter that is at least 5% smaller than a diameter of the proximal neck region of the aneurysm.

17. The method of claim 12,
wherein filling the first filling structure includes filling the first filling structure with a polymer that sets after the one or more portions of the first filling structure have protruded through the one or more openings so as to lock the first filling structure to the anchor device.

18. A system for deployment in a blood vessel, the system comprising:
an anchor device comprising:
a stent; and
a suture loop that joins distal end portions of the stent; and
a filling structure;
wherein the stent is expandable to an expanded state,
wherein the filling structure is at least partially insertable through the suture loop to an area within the stent when the stent is in the expanded state,
wherein the anchor device includes barbs that are attachable to a wall of an aorta above renal arteries, and
wherein the anchor device has a size such that at least a portion of the filling structure protrudes through openings in the anchor device to contact a wall of the aorta below the renal arteries when the barbs have been attached to the aorta above the renal arteries and the filling structure has been at least partially inserted through the suture loop and has been filled.

* * * * *